US012746292B2

(12) United States Patent
Keenan

(10) Patent No.: US 12,746,292 B2
(45) Date of Patent: Sep. 29, 2026

(54) METHODS OF PRODUCING MICROBUBBLE DRUG CONJUGATES, VIRAL GENE THERAPY MICROBUBBLE CONJUGATES AND TARGETED MICROBUBBLES

(71) Applicant: James Alexander Keenan, Ottawa (CA)

(72) Inventor: James Alexander Keenan, Ottawa (CA)

( * ) Notice: Subject to any disclaimer, the term of this patent is extended or adjusted under 35 U.S.C. 154(b) by 0 days.

(21) Appl. No.: 17/988,736

(22) Filed: Nov. 16, 2022

(65) Prior Publication Data

US 2025/0177557 A1 Jun. 5, 2025

Related U.S. Application Data

(60) Provisional application No. 63/281,215, filed on Nov. 19, 2021.

(51) Int. Cl.

| | |
|---|---|
| ***A61K 47/69*** | (2017.01) |
| ***A61K 41/00*** | (2020.01) |
| ***A61K 47/68*** | (2017.01) |
| ***A61K 48/00*** | (2006.01) |

(52) U.S. Cl.
CPC ...... *A61K 47/6913* (2017.08); *A61K 41/0028* (2013.01); *A61K 47/6839* (2017.08); *A61K 47/6849* (2017.08); *A61K 48/0041* (2013.01)

(58) Field of Classification Search
CPC ............ A61K 47/6913; A61K 47/6839; A61K 47/6849; A61K 41/0028; A61K 48/0041
See application file for complete search history.

(56) References Cited

U.S. PATENT DOCUMENTS 6,638,767 B2 * 10/2003 Unger .................... A61P 11/00 435/458
2018/0344872 A1 * 12/2018 Callan ................. A61K 47/545

* cited by examiner

*Primary Examiner* — Michael P Cohen

(57) ABSTRACT

The present invention relates to methods of producing microbubble drug conjugates, viral gene therapy microbubble drug conjugates, and disease-targeting microbubbles, for clinical and preclinical ultrasound-mediated therapeutic and diagnostic applications. It includes methods to produce viral vector gene therapy microbubble drug conjugates with antibody linkers conjugated to lipid shelled microbubbles that both bind to and neutralize viral vectors such that the viral gene therapy can transduce and effect permanent genetic changes only after ultrasound is used to disassociate the viral gene therapy from microbubbles at diseased regions of the body.

3 Claims, 7 Drawing Sheets

METHODS OF PRODUCING MICROBUBBLE DRUG CONJUGATES, VIRAL GENE THERAPY MICROBUBBLE CONJUGATES AND TARGETED MICROBUBBLES

FIELD OF THE INVENTION

The present invention relates to methods of producing therapeutic or diagnostic microbubbles:

1. Viral gene therapy microbubble drug conjugates (MDCs) using antibodies with binding specificity to different viral vectors (AAV2, AAV9, adenovirus, etc.) covalently conjugated to the lipids that form the microbubble shells, generating microbubbles with the antibody linkers conjugated to the lipid shells, followed by incubation of viral gene therapy to bind to the MDC surfaces.
2. Biologic drug (antibodies, proteins, ligands, bispecific T cell engaging antibodies, others) or viral gene therapy microbubble drug conjugates on demand or using other means such, for example, sonication of an enclosed lipid solution and gas,
3. Disease-targeting microbubbles to enhance ultrasound diagnosis.

These methods will be used with ultrasound and/or focused ultrasound mediated therapy or diagnosis.

The present invention also includes methods to produce immunotherapy anti-drug antibody (or neutralizing antibody) loaded liposomes that may be administered post MDC treatment in order to mitigate immune-related adverse effects in the liver. The present invention includes methods to produce MDCs with antibody linkers with binding specificity to different viral vector gene therapies as well as antibody linkers.

Focused ultrasound can be used to target diseased regions of the body and release biologic drugs or viral gene therapy from MDCs for local delivery.

The present invention includes methods to produce MDCs with viral vector antibody linkers that also neutralize the viral vectors in order to limit transduction and permanent genetic changes to diseased regions of the body targeted by focused ultrasound. More specifically, the present invention relates to methods of producing targeted microbubbles and microbubble drug conjugates for clinical applications.

BACKGROUND OF THE INVENTION

Gas-filled microbubbles are useful in various types of clinical diagnostic applications, including molecular diagnostics. In these applications, microbubbles are particularly useful for diagnosis of diseases with vascular-expressing targets, such as cancer or cardiovascular•diseases. Microbubble mediated therapy•techniques have been developed and have progressed to early stage clinical use. (Ferrara K et al. (2007). Annu. Rev. Biomed. Eng. 9:415-47 and Frenkel P, (2002) Ultrasound in Medicine and Biology and Anderson C R, Klibanov A L., et al (2010) scVEGF microbubble ultrasound contrast agents: a novel probe for ultrasound molecular imaging of tumor angiogenesis. Invest Radiol. 45:579-585.)

Microbubbles are micrometer sized bubbles that are used for contrast enhancement during ultrasound imaging. The microbubbles comprise a gas core (e.g. air or perfluorcarbon gas) encapsulated in a lipid, albumin, or polymer-based shell. When ultrasound is applied to microbubbles circulating in the body, they oscillate and reflect the ultrasound waves resulting in contrast enhancement relative to the surrounding tissue. Although microbubbles have proven useful for clinical imaging applications, the ability for molecular imaging or targeted therapy is under development (Klibanov A, (2005) Bioconjugate Chem. 2005, 16, 9-17) because they have a short half-life in circulation and do not retain in diseased tissues.

The development of targeted microbubbles (Pillai R, et al, (2010) Bioconjug Chem. 21, 556-562.) represents a technology that may increase the utility of microbubbles for targeted imaging and therapy applications. For instance, when microbubbles are combined with a disease-specific targeting biologic (i.e. protein, antibody, peptide, etc), molecular imaging of a specific disease process is possible. As an added benefit, the appropriate targeting biologic can allow for the delivery of more microbubbles to the diseased area, thus improving the therapeutic effect. This is achieved by bursting the microbubbles in the body to open cellular barriers via sonoporation effects.

Other microbubble therapeutic effects have been developed. Ultrasound can induce rapid expansion and contraction of microbubbles to mechanically impact tumor vasculature in order to slow or halt tumor blood flow. This effect has shown considerable synergy with chemotherapy [Goertz, D. E.; Todorova, M.; Mortazavi, O.; Agache, V.; Chen, B.; Karshafian, R.; Hynynen, K. Antitumor effects of combining docetaxel (taxotere) with the antivascular action of ultrasound stimulated microbubbles. PLOS. ONE 7: e52307; 2012.] to increase tumor reduction and enhance survival.

Tumor targeting microbubbles that retain in tumor blood vessels would have clinical advantages over non-targeted microbubbles in terms of enhanced tumor vascular damage and that they can be used with conventional, non-focused ultrasound equipment rather than specialized focused ultrasound.

Only about 0.1% of biologic drugs such as antibodies, proteins, and bi-specific T cell engaging antibodies (BiTEs) administered intravenously (IV) cross the blood brain barrier (BBB). Current BBB delivery options for biologics have significant drawbacks: saturation IV•dosing systemic side effects, direct surgical infusion invasiveness, and receptor mediated 'Trojan horse' delivery with limited dose delivered to the brain. These limitations are a key reason why, for example, clinical trials for Alzheimer's and Parkinson's disease with biologics have failed. (Bartus R., et al Mol Ther 2014)

For example, current brain delivery methods for Parkinson's Disease (PD) rely on direct injections to the to the striatum (ST) using catheter and pump systems or needles that require invasive surgery (Moreno, M. J., et al. (2006) Glia 53, 845-857) and also rely on retrograde transport to the substantia nigra (SN). Both the ST and SN need effective drug delivery in order to treat PD.

Invasive delivery clinical trials have only been approved for advanced PD patients with limited number of dopamine neurons available to treat. While AAV/NRTN (CERE-120) clinical trials did not meet clinical endpoints they did demonstrate (Couch, J. A., et al. (2013) Sci. Transl. Med. 5, 1-12):

- long-term (4-5 years after operation) biologically active protein expression via immunohistochemistry in tissue from post-mortem brains of treated subjects
- safe delivery of AAV2 to the brain
- very little NRTN in the SN of autopsy tissue; it appeared that neuronal pathology in the aged human PD brain was more severe than that of animal models, preventing NRTN transport from the putamen (ST) to the SN phase 2b data suggests earlier-stage PD subjects (5 or fewer years postdiagnosis) showed much greater clinical benefit from AAV-NRTN than did those treated at 10 or more years postdiagnosis This clinical evidence suggests that non-invasive delivery throughout the SN and ST for early stage patients with more healthy neurons available for treatment, better transport, and less-pathological anti-neurotrophic molecular cascades is critical for an effective treatment of Parkinson's Disease.

Non-invasive, targeted blood brain barrier drug delivery can be achieved by combining circulating microbubbles with MR guided focused ultrasound. The focused ultrasound is capable of targeting deep seated brain tissue to open up precise regions of the blood brain barrier in a safe, reversible and repeatable manner in both rats and primates [McDannold, N.; Arvanitis, C. D.; Vykhodtseva, N.; Livingstone, M. S. Temporary disruption of the blood-brain barrier by use of ultrasound and microbubbles: safety and efficacy evaluation in rhesus macaques. Cancer Res. 72:3652-3663; 2012, and Burgess, A.; Hynynen, K. Noninvasive and targeted drug delivery to the brain using focused ultrasound. ACS Chem. Neurosci. 4:519-526; 2013] and patients [McDannold, N.; Clement, G. T.; Black, P.; Jolesz, F.; Hynynen, K. Transcranial magnetic resonance imaging-guided focused ultrasound surgery of brain tumors: initial findings in 3 patients. Neurosurgery 66:323-332; 2010].

Experimental evidence suggests that the interaction between the ultrasound, microbubbles and brain vasculature leads to mechanical forces that temporarily open up tight junctions and induces active transport processes (Burgess, A.; Hynynen, K. et al, Focused ultrasound-mediated drug delivery through the blood-brain barrier Expert Rev Neurother. 15 (5): 477-491) 4:519-526; 2015) allowing increased uptake of systemic drugs to the brain parenchyma. It is not possible to open the BBB safely using FUS alone as microbubbles are required to do so at low acoustic pressures.

Clinical trials have been done to establish the safety of temporarily opening the blood brain barrier with focused ultrasound and microbubbles for glioblastoma, Alzheimer's Disease, ALS, Parkinson's Disease, and breast cancer brain met patients (Lipsman N, Hynynen K et al (2019) 'Blood-Brain Barrier Opening in Primary Brain Tumors with Non-invasive MR-Guided Focused Ultrasound: A Clinical Safety and Feasibility Study' Sci Rep. 2019 Jan. 23; 9(1):321). The goal is to follow these safety trials with targeted, non-invasive, drug delivery to the brain to treat CNS disorders.

Clinically, ultrasound-transducers implanted in glioblastoma patient's skulls have been used to increase the delivery of small molecule chemotherapy drugs (NCT03744026).

While not directly equivalent to focused ultrasound and microbubble BBB opening this trial indicates that repeated ultrasound sonications to the brains of glioblastoma patients is being shown to be safe.

The focused ultrasound and microbubble BBB opening persists for a few hours sufficient for small molecule drug delivery but for larger, high impact therapeutics such as AAV gene therapies and antibodies it is believed that most of the delivery occurs during the few minutes of sonication. Therefore microbubble drug conjugates (MDCs) offer the advantage for clinical translation in that 'large' AAV gene therapies are proximal to the BBB opening for higher dose delivery.

Checkpoint inhibitors and other immunotherapies have been wonder drugs for some cancer patients but the overall response rate is only about 20%. There is considerable clinical interest in combining immunotherapy drugs and in combining immunotherapies with other therapies such as radiotherapy. While combination treatments have increased the number of patients responding to treatment they typically also increase adverse effects. For example, Incidence of grade 3 or −4 treatment-related AEs were 59% in the nivolumab plus ipilimumab group, 21% in the nivolumab group, and 28% in the ipilimumab group. (Minglei Zhou, et al, Asia Pacific Journal of Clinical Oncology, 2020)

Immunotherapy biologics such as checkpoint inhibitor antibodies (Keytruda, Tecentriq, others) and oncolytic viruses do not effectively cross the BBB and clinical trials as monotherapies or as combination therapy with chemotherapy regularly exclude patients with brain metastases: Tecentriq breast cancer clinical trial NCT03125902, Keytruda with or without Talimogene laperparepvec oncolytic virus melanoma trial NCT02263508, Talimogene laperparepvec for triple negative breast cancer NCT02779855; and others.

The most successful immunotherapies for brain mets include a recent Keytruda trial with response in about one third of lung cancer patients and combination immunotherapies such as Yervoy and Opdivo with responses in about half the brain metastasis patient population but with adverse effects, some quite severe, in about one quarter of the patients.

Thus here remains a need in the art for a method to a) effectively and non-invasively increase immunotherapy concentrations in brain met tumors, b) further boost immunotherapy efficacy, and c) mitigate immunotherapy adverse effects.

Ultrasound manipulation of circulating microbubbles can increase immunotherapy efficacy without the added toxicity associated with combining other drugs or treatments:

Promote the release of tumor antigens, modulate the tumor microenvironment, and increase cytotoxic T-cells (Lui et al (J Trans Medicine, 2012) and Hunt et al (J Ultrasound Med, 2015)

1st clinical trial of Keytruda with focused ultrasound ablation and immune response promotion to treat breast cancer October 2017

Ultrasound manipulation of circulating microbubbles to disrupt tumor blood flow has also been shown to significantly boost immunotherapy efficacy. (Sharshi Bulner, Aaron Prodeus, Kullervo Hynynen, and David E. Goertz, 'Enhancing Checkpoint Inhibitor Therapy with Ultrasound Stimulated Microbubbles' Ultrasound in Med. & Biol., Vol. 00, No. 00, pp. 1_14, 2018).

Importantly, successful FUS/MDC tumor blood vessel damage can be verified using ultrasound imaging (Goertz D, et al, PLOS-One Volume 7 Issue 12, 2012) a few hours after the procedure to provide 'biomarker like' short term confirmation of treatment success without waiting weeks to verify tumor reduction.

In addition to BBB delivery of immunotherapy to treat brain mets serious unmet needs such as colorectal liver mets could potentially be managed by FUS/MDC targeted immunotherapy delivery to liver mets along with FUS/MDC tumor vasculature disruption efficacy•boost.

Ultrasound enhanced drug delivery is practiced clinically to treat deep vein thrombosis and peripheral arterial occlusion (Ekos Corporation, Bothwell Washington). Localized catheter delivery of tissue plasminogen activator (tPA) drug is enhanced with catheter mounted ultrasound. Microbubbles further amplify ultrasound drug delivery effects. Therefore thrombos dissolving procedures would be faster and more effective with local delivery of tPa conjugated to microbubbles with ultrasound.

Loading drugs onto microbubbles has four advantages over sequential administration of drugs and microbubbles. A higher dose of the drug is delivered to the area of interest, (Wang, F., et al. (2012) PLOS. ONE 7, e52925), enhanced drug perfusion and retention in diseased regions, systemic side effects are mitigated as unused drug is cleared along with the deflated microbubble lipid shells in the liver by Kupffer cells, and drug conjugation to MDCs will promote in vivo stability of biologics such as proteins that tend to degrade quickly in the bloodstream.

There are currently three main bioconjugation techniques for attaching proteins to microbubbles, each with its own clinical challenges. Electrostatic-adsorption allows for association of charged proteins to the microbubble surface. For example, negatively charged plasma DNA has been attached to the cationic microbubbles (Phillips et al, 2010); in another example, proteins with a positively-charged histidine tag have been linked to Ni-NTA containing lipid vesicles (Platt et al, 2010). However, this type of linkage often results in inefficient amounts of proteins being linked to the microbubble shell; additionally, this type of linkage is not stable in vivo, as the proteins are quickly displaced by plasma proteins.

Non-covalent linkages have also been used for microbubbles. For example, the avidin-biotin technology is the main linkage used in currently published studies (Lindner, 2001). However, there are recognized immunogenic concerns of this linkage in humans (Meyer et al, 2001). For this reason, this linkage is not deemed clinically translatable, but may be useful for preclinical studies.

Another common method for associating protein molecules to microbubbles is by covalent linkage (also referred to as chemical conjugation). Chemical conjugation techniques are best to use for in vivo studies as they are stable in the blood and have proven successful when linking biologics to lipid. A variety of standard chemical conjugation reactions have been utilized in the literature, including attaching a peptide or protein via carbodiimide chemistry (Palmowski et al, 2008) or stable thioether bond chemistry (Anderson et al, 2010); polymer spacers of various length, such as PEG, may be used to maintain distance between the protein and the microbubble shell (Kim et al, 2000).

Unfortunately, post-formation attachment of biologics to gas-containing microbubbles via covalent linkage is problematic, as the integrity of the microbubble 'gas' core can be compromised during the reaction and/or purification steps; this results in insufficient contrast for ultrasound imaging. Post-formulation attachment of biologics may also result in less consistent drug loading per microbubble as well as reduced loading efficiency both of which reduce treatment efficacy. The on-demand MDC generation (Reference U.S. Pat. No. 8,257,338) also produces microbubbles immediately after formation at around 20 microns that quickly shrink and stabilize to 2 micron diameter. Pre loading the biologic may be a factor in increasing drug loading per MDC. Additionally chemical conjugation and purification requires specialized chemical skills that may not be readily available in a clinical setting. While attempts have been made to pre-attach peptides directly to lipids in organic solvents (Pillai et al, 2010) prior to microbubble formation, success is limited due to susceptibility of folded proteins to denaturation caused by the organic solvents involved in the production process.

Another limitation for current microbubble conjugation techniques is the type of compounds that can be combined, typically simple ligands and peptides. A need exists to combine a wider range of therapies: complex 3-D folded antibodies, immunotherapy antibodies, bispecific T cell engaging antibodies, and others.

Microbubbles used as diagnostic ultrasound contrast agents may undergo a lyophilization or freeze-drying process to enhance stability during storage and shipping until the microbubbles are reconstituted in a hospital pharmacy with sterile diluent. However, lyophilization is expensive and requires complex and costly equipment. In addition, losses of up to 50% can occur in the process and if it is used with microbubble drug conjugates losses featuring expensive biologics lead to excessive costs.

Artenga Inc.'s current techniques disclosed in U.S. Pat. Nos. 8,679,051, 8,257,338 permit stable shipment and storage of sterile, disposable microbubble cartridges prefilled with microbubble solution and gas that can be reconstituted on demand using a tabletop microbubble generator device for a clinically scalable means to avoid lyophilization costs. Thus there remains a need in the art for a method to chemically conjugate biologics without immunogenic linkers using this on demand microbubble generation.

Gene-based therapeutics have great potential to induce target genes for extended periods of time (Ozcan, G., et al. (2015) Adv. Drug Deliv. Rev. 87, 108-119.). A major hurdle limiting the use of this technology is the lack of methods to safely and efficiently deliver these molecules to target cells/tissues. In the free form, gene-based molecules have a very short half-life in physiological conditions, owing to their vulnerability for degradation by endogenous nucleases. Therefore, they need macromolecular carriers (vectors) that will not only protect them from degradation in the biological milieu, but also steer them to desired cells/tissues and facilitate their cellular entry.

Currently, lipid carriers are extensively being explored as potential delivery vehicles for protein and gene-based therapeutics (Moreno, M. J., et al. (2013) Neoplasia 15, 554-567. Joyce, J. A., et al. (2004) Cancer Cell 5, 443-453.) Lipid carriers can be formulated to be non-toxic, transport high payloads, and facilitate the release of biologics into the cellular cytoplasm.

Conjugation of viral vector gene therapy to lipid shelled microbubbles has the potential to address rapid renal clearance, poor cellular uptake, degradation by endogenous enzymes and immune response after systemic administration.

However, the blood brain barrier impedes lipid-carrier gene therapy treatment of CNS disorders. The available options are:

1. Saturation dose systemic administration with the risks of off target dosing and adverse effects
2. Invasive surgical procedures to infuse gene therapy with transcranial catheters or needles which limit trials to advanced case patients and are unlikely to achieve long term management of indications such as diffuse brain cancers
3. AAV9 gene therapy does penetrate the BBB but has the following drawbacks:
   - A propensity to induce an immune response that can require an immuno-suppression regime which would limit clinical use (for example, NCT04127578 administration of Sirolimus and Prednisone immuno-suppressants)
   - AAV9 delivery effects permanent genetic changes throughout the brain without local targeting of diseased regions
   - AAV9 may require intrathecal infusion into the lumbar spinal cord or intracisternal administration versus non-invasive intravenous (IV) administration 4. Bracco PLC is developing gene therapy MDCs using 'naked', naturally anionic DNA electrostatically bound to cationic microbubbles. This technology could be used with FUS to open the BBB but relies on microbubble/FUS interaction to promote DNA transduction.

In addition, pre-existing immunity against specific adeno-associated virus (AAV) serotypes or other viral gene therapies can result in the exclusion of patients from clinical trials. For example, an average prevalence for anti-AAV8 (~40%) and anti-AAV5 (~30%) neutralizing antibodies (Kruzik A., Mol Ther Methods Clin Dev. 2019 Sep. 13; 14:126-133). Pre-existing neutralizing antibodies can be avoided for CNS gene therapy using direct injection into the brain or spinal cord but invasive delivery methods may preclude gene therapy use in early stage patients. Hence, there exists a need to develop a flexible gene therapy method to use a variety of AAV serotypes and other methods to maximize the treatable patient population.

Thus, there remains a need in the art for a cost effective, controllable process to produce microbubble drug conjugates for viral gene therapy in order to enable focused ultrasound mediated treatments that feature:

1. Non-invasive, high dose delivery precisely targeted to diseased brain regions
2. Viral vector delivery for better transduction and efficacy than is possible with microbubble and focused ultrasound delivery of naked DNA
3. The use of any viral delivery technology (adenoviral, lentiviral, HSV, AAV, etc) including a variety of AAV serotypes such as AAV2 which have a limited immune response in order to avoid AAV9 immuno-suppression regimes
4. Delivery to multiple diseased regions treated in a single procedure
5. Liver clearance of unused gene therapy to avoid systemic adverse effects There also remains a need in the art to develop MDCs with antibody linkers that bind to as well as neutralize viral vectors to prevent transduction unless the viral gene therapy is disassociated (released) from the MDCs using focused ultrasound. This would limit permanent genetic changes to diseased regions of the brain or other organs targeted by FUS with unused viral gene therapy MDCs cleared in the liver unable to transduce.

SUMMARY OF THE INVENTION

The present invention relates to methods of producing microbubble drug conjugates (MDCs) and disease targeting•microbubbles using microbubble generation•methods disclosed in U.S. Pat. Nos. 8,679,051, 8,257,338 as well as viral gene therapy MDCs generated through a variety of methods. It includes viral gene therapy MDCs with antibody linkers covalently conjugated to the MDC's lipid shells that both bind to and neutralize viral vectors in order to prevent transduction and permanent genetic changes while the MDC circulates in the body and is cleared in the liver. This binding and neutralizing viral gene therapy MDC thus permits precision targeted delivery using focused ultrasound to disassociate (release) the viral gene therapy from the MDCs for transduction and treatment of diseased regions only. More specifically, the present invention relates to methods of microbubble drug conjugates and targeted microbubbles for clinical applications.

Biologics are covalently attached to functionalized, stable lipid vesicles in aqueous buffers prior to gas microbubble formation. In this method, the biologic is attached to amine-PEG, carboxyl-PEG, azide-PEG, or other functionalized lipid vesicles prior to conversion to microbubbles. The lipid vesicles can be purified of unbound biologics before being converted to MDCs.

The inventor then developed novel methods and modified microbubble generation equipment in order to incorporate the amine-PEG-DPSE and/or amine-PEG-DPSE-biologic in lipid vesicles while maintaining or improving desirable microbubble concentrations and achieving desired in vivo persistence of the microbubbles.

Using this method, MDCs and targeted microbubbles may be produced "on demand" in the clinic without the requiring specialized chemical knowledge or purification steps. Additionally, this approach avoids the risk of impacting the integrity of the gas contained within the microbubble when the biologic is conjugated post-microbubble formation.

Custom antibody linkers were developed that preferentially bind to adeno-associated virus (AAV) vectors with controllably varying binding affinities. Linkers specific to AAV2 were developed and the technique can be used to develop linkers specific to other serotypes (AAV1, AAV9 etc.) and other viral vectors (adenovirus, oncolytic viruses, retrovirus, herpesvirus, etc.) These AAV viral vector linkers were covalently conjugated to functionalized lipid vesicles. Microbubbles with antibody linkers conjugated to the lipid shells were then generated and AAV gene therapy added to the solution and incubated to form viral gene therapy microbubble drug conjugates. Centrifugation may be performed after conjugation to remove viral gene therapy not bound to microbubbles.

In vitro experiments of these MDCs with linkers of varying binding strengths were done using an ultrasound flow chamber and cell bed apparatus as shown in Example 13. We demonstrated that FUS sonications relevant to clinical BBB opening parameters can be used to disassociate AAV2-GFP from MDCs for transduction. The AAV antibody linkers had sufficient binding affinity to ensure that the viral gene therapy remains conjugated to the MDCs in vivo and is hence cleared in the liver to avoid systemic delivery but can be released from the MDCs for localized delivery to diseased brain regions (or other organs) using ultrasound.

In vivo experiments using AAV2-SIRT3 MDCs demonstrated SIRT3 expression in the striatum of healthy rodents. SIRT3 is a Parkinson's Disease neuroprotective gene therapy and so demonstrated in vivo, non-invasive, targeted BBB delivery of a viral gene therapy to a brain region affected by a CNS disorder.

The lipid shells and drug of MDCs not targeted by focused ultrasound and used to deliver drugs to diseased regions of the body are cleared in the liver. In a preferred embodiment of the gene therapy MDC invention a viral binding/neutralizing antibody linker that preferentially binds to and neutralizes different viral vectors is developed. Focused ultrasound will release the viral gene therapy from MDCs at diseased regions of the body for effective transduction and treatment. The neutralizing linker will prevent the remaining MDCs in circulation and then cleared in the liver from transducing and causing permanent genetic changes in healthy tissue.

Other aspects and features of the present disclosure will become apparent to those ordinarily skilled in the art upon review of the following description of specific embodiments in conjunction with the accompanying figures.

BRIEF DESCRIPTION OF THE DRAWINGS

These and other features of the invention will now be described by way of example, with reference to the appended drawings, wherein.

DESCRIPTION OF PREFERRED EMBODIMENTS

The present invention relates to methods of producing microbubble drug conjugates (MDCs), viral gene therapy MDCs, and targeted microbubbles. More specifically, the present invention relates to methods of producing MDCs and targeted microbubbles for clinical applications.

Biologics with therapeutic or selective targeting capabilities are to be added in a covalent manner to lipid vesicles, prior to microbubble formation. In this way, the addition of biologics does not impact the integrity of the gas contained within the microbubble. To do this, pre-attachment of biologics to, for example, amine-PEG, carboxyl-PEG, or azide-PEG functionalized lipid vesicles prior to conversion to microbubbles is a viable solution to develop clinically useful MDCs or targeted microbubbles ready for injection. This sequence for producing these will allow for MDCs and targeted microbubbles to be produced in the clinic without the requirement of chemistry knowledge.

The choice of linker can consist of any functionalized lipid suitable for conjugation to biologics, including amines, carboxy, biotin, maleimide, hydrazide, or azide or other click chemistry methods. These lipid vesicles can encompass any type of unilamellar or multilamellar vesicle, liposome, micelle, bicelle and including those derived from living cells such as exosomes or microvesicles. If required, the lipid vesicles are then purified of unbound biologics before being converted to microbubbles by incorporating gas into the vesicles with various standard mixing or alternative microbubble formation procedures. The lipid vesicle solution can be supplied to clinicians in a vial, cartridge, etc., which also contains perfluorocarbon gas. This vial can then be used on demand and to produce gas-filled microbubble drug conjugates or targeted microbubbles ready for injection when it is processed using various known procedures for microbubble formation.

Figure 1:
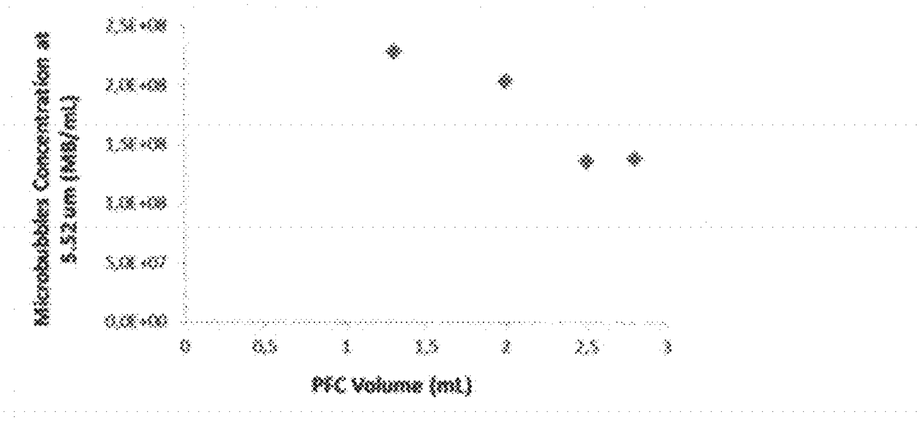
FIG. 1 Microbubble Coulter counter concentration at different PFC (perfluorocarbon) gas volumes FIG. 2 Microbubble concentrations using different microfluidics for microbubble generation (red and purple capillary tubes) (Reference U.S. Pat. Nos. 8,679,051, 8,257,338), at varying air volumes, and varying quantities of DSPC lipid (40-70 mg) in the microbubble shell formulation.

This strategy can allow for an easy production of MDCs and targeted microbubbles ready for clinical use To do this will require the following steps using, for example, amine-PEG (see FIG. 1):

1) Incorporation of amine-PEG-lipids into lipid formulation at various molar ratios in organic solvents.
2) After evaporation of the organic solvents, the lipids will be re-hydrated using PBS, pH 7.4 to create lipid vesicles.
3) Chemical conjugation of biologics using their c-terminal carboxy group to the amine groups that are incorporated on the lipid vesicles.
4) Purification of unbound biologics from the antibody-bound lipid vesicles
5) Adding targeted-lipid vesicles to a cartridge, which also contains surfactants and gas.
6) Cartridge is then mixed, which will push gas into targeted lipid vesicles to produce targeted microbubbles. This mixing can be done in an automated or manual manner by various known methods.

The use of chemical attachment of biologics to the lipid vesicles stage rather than at the individual lipid stage or at the post microbubble formation stage allows for microbubble drug conjugates (MDCs) to be produced "on demand" in the clinic. In the clinic, an individual can convert biologic drug-lipid vesicles contained within a vial or cartridge to MDCs without impacting microbubble formation or the biologics' bioactiviy. This strategy would allow MDCs to be produced on demand in the clinic in one step. Vials containing biologics, lipid vesicles, and gas can be safely stored in the fridge until needed without lyophilization and reconstitution. When MDCs are required, a cartridge is mixed by various known methods for microbubble formation without compromising sterility and MDCs or targeted microbubbles are generated automatically and are ready for injection into patients. The ease of generation of MDCs or targeted-microbubbles in this manner, without the requirement of chemistry knowledge post microbubble formation makes clinical use of this technology feasible.

The present invention will be further illustrated in the following examples. However, it is to be understood that these examples are for illustrative purposes only and should not be used to limit the scope of the present invention in any manner.

TABLE 1

List of Examples

| Example | Embodiment |
|---|---|
| 1 | Production of lipid vesicles |
| 2 | Microbubble production and characterization |
| 3 | Cy5.5 labeling of lipid vesicle solution |
| 4 | Conjugation of biologics to lipid vesicles |
| 5 | Microbubble formation from labeled lipid vesicles |
| 6 | Conjugated microbubble characterization |
| 7 | Binding of conjugated microbubbles |
| 8 | Production of Microbubble Drug Conjugates or Targeted Microbubbles |
| 9 | Bioactivity Confirmation of Microbubble Drug Conjugates |
| 10 | Microbubble Drug Conjugate and Focused Ultrasound Blood Brain Barrier Opening for Non-invasive, Targeted Drug Delivery to the Brain. |
| 11 | Production of Viral Vector Gene Therapy Antibody Linkers |
| 12 | Production and Characterization of Viral Gene Therapy Microbubble Drug Conjugates with Antibody Linkers |
| 13 | Viral Gene Therapy Microbubble Drug Conjugate Non-invasive, Targeted Blood Brain Barrier Delivery |
| 14 | Production and Treatment Methods for Viral Gene Therapy MDCs With Neutralizing Antibody Linkers |
| 15 | Production of Small Molecule Drug and Microbubble Conjugates |
| 16 | Production of Disease-targeting Microbubbles for Diagnosis with in vitro and in vivo characterization |

Example 1: Production of Lipid Vesicles

Lipid vesicles were formed that incorporate amine-PEG-lipids or in various molar ratios. These vesicles will be used in subsequent examples; where biologic molecules are conjugated to the lipid vesicles prior to microbubble formation.

Lipid vesicles were formed using methods well-known in the art. Briefly, a lipid mixture (i.e. amino functionalized PEG-DSPE lipid, phosphotidylcholine lipids or other lipids suitable to generate lipid vesicles such as DSPC, DBPC, others) was dissolved in chloroform to achieve desired lipid composition and ratio. The lipids were then vortexed. The chloroform was evaporated overnight under reduced pressure and elevated temperature (>45° C.) using a Vacufuge™ to ensure complete removal of the chloroform. A thin lipid film was then rehydrated with PBS, pH 7.4 at 60° C. using a hot water bath to create a lipid solution comprising lipid vesicles with an aqueous center.

A lipid mixture of DBPC (1,2-Distearoyl-sn-glycero-3-phosphocholine) plus DSPE-PEG (2000) was formed to increase the in vivo persistence of the MDCs. Extended in vivo persistence improves ultrasound and microbubble therapies such as non-invasive, targeted, temporary opening of the blood brain barrier for drug delivery as well as tumor vascular disruption to boost immunotherapy and chemotherapy efficacy. Extended in vivo persistence also permits increased drug concentration locally delivered to diseased regions A lipid mixture of DBPC and DSPE-PEG-Azide (2000) was developed to permit microbubble drug conjugates using click chemistry (also described in Example 3). The utility of using click chemistry versus covalent chemical conjugation is to minimize drug losses during the conjugation process.

Example 2: Microbubble Production and Characterization

The lipid vesicles of Example 1 were converted to microbubbles. The microbubble solutions were then characterized to determine the total microbubble count and their size distribution.

The lipid vesicles are converted to microbubbles by either piezoelectric transducer 5 agitation of sealed liposome solution and gas, electrolysis and ultrasound generation, or use of a microbubble generation apparatus through reciprocally driving the drug-liposome solution and gas through a bubble generation module (Reference U.S. Pat. No. 8,257,338), Microbubble characterization results are shown in Tables 2 and 3. Results indicate that the addition of 1×, 2×, or 3× amine-PEG-DSPE linker lipid into the lipid vesicles did not impact the gas microbubble formation, size, or concentration of generated microbubbles.

TABLE 2

Summary comparison of total microbubble counts/ml of various lipid microbubbles containing 1X, 2X or 3X PEG amine linker.

| PEG amine | Microbubble Solution Dilution | Total Microbubble Counts/ml |
|---|---|---|
| 1X | 0.8 ml MB solution, 1.2 ml PBS, pH 7.4 | $5.34 \times 10^8$ |
| 2X | 0.8 ml MB solution, 1.2 ml PBS, pH 7.4 | $2.60 \times 10^8$ - run 1<br>$2.89 \times 10^8$ - run 2 |
| 3X | 0.8 ml MB solution, 1.2 ml PBS, pH 7.4 | $4.41 \times 10^8$ - run 1<br>$5.44 \times 10^8$ - run 2<br>$3.96 \times 10^8$ - run 3 |

TABLE 3

Coulter counter results of microbubble size distribution and concentration in the sample with 1X, 2X, 3X PEG amine linker.

| Size μM | 1X [C]/mL | 2X - run 1 [C]/mL | 2X - run 2 [C]/mL | 3X - run 1 [C]/mL | 3X - run 2 [C]/mL | 3X - run 3 [C]/mL |
|---|---|---|---|---|---|---|
| 0.75-1.00 | $1.953 \times 10^8$ | $2.836 \times 10^8$ | $1.640 \times 10^8$ | $2.836 \times 10^8$ | $2.650 \times 10^8$ | $2.428 \times 10^8$ |
| 1.01-2.00 | $2.421 \times 10^8$ | $1.163 \times 10^8$ | $7.354 \times 10^7$ | $1.163 \times 10^8$ | $2.074 \times 10^8$ | $1.077 \times 10^8$ |
| 2.01-3.00 | $6.719 \times 10^7$ | $3.364 \times 10^7$ | $1.874 \times 10^7$ | $3.364 \times 10^7$ | $5.184 \times 10^7$ | $3.677 \times 10^7$ |
| 3.01-4.00 | $8.407 \times 10^6$ | $6.482 \times 10^6$ | $3.057 \times 10^6$ | $6.482 \times 10^6$ | $1.618 \times 10^7$ | $7.912 \times 10^6$ |
| 4.01-5.00 | $3.500 \times 10^5$ | $5.499 \times 10^5$ | $1.692 \times 10^5$ | $5.499 \times 10^5$ | $3.189 \times 10^6$ | $6.747 \times 10^5$ |
| 5.01-6.00 | $1.869 \times 10^4$ | $2.475 \times 10^4$ | $1.818 \times 10^4$ | $2.475 \times 10^4$ | $3.732 \times 10^5$ | $6.111 \times 10^4$ |

TABLE 3-continued

Coulter counter results of microbubble size distribution and concentration in the sample with 1X, 2X, 3X PEG amine linker.

| Size μM | 1X [C]/mL | 2X - run 1 [C]/mL | 2X - run 2 [C]/mL | 3X - run 1 [C]/mL | 3X - run 2 [C]/mL | 3X - run 3 [C]/mL |
|---|---|---|---|---|---|---|
| 6.01-7.00 | $5.555 \times 10^3$ | $7.575 \times 10^3$ | $3.535 \times 10^3$ | $7.575 \times 10^3$ | $6.262 \times 10^4$ | $8.080 \times 10^3$ |
| 7.01-15.00 | $6.575 \times 10^3$ | $3.030 \times 10^3$ | $1.010 \times 10^3$ | $3.030 \times 10^3$ | $1.263 \times 10^4$ | $6.565 \times 10^3$ |
| 15.01-30.00 | $3.030 \times 10^3$ | 0.000 | $1.010 \times 10^3$ | 0.000 | $5.050 \times 10^2$ | 0.000 |

Figure 2:
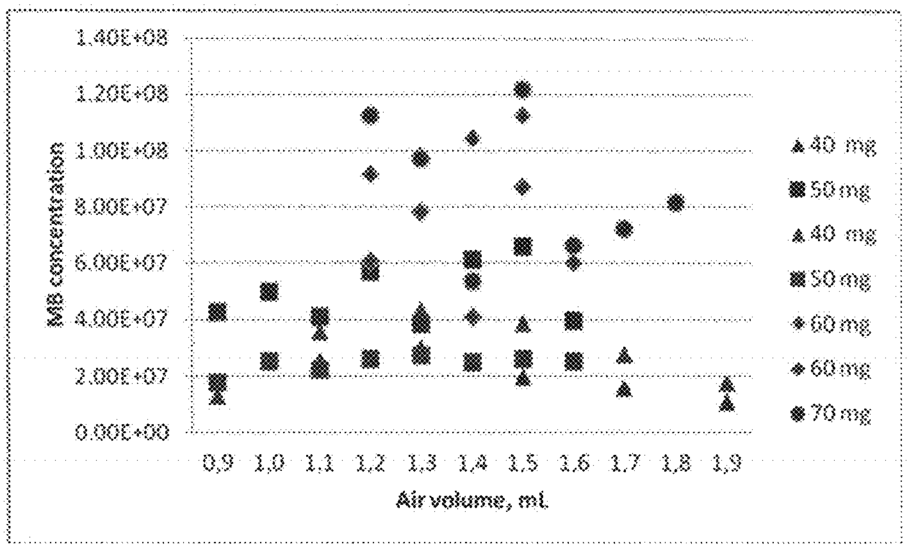
Figure 3:
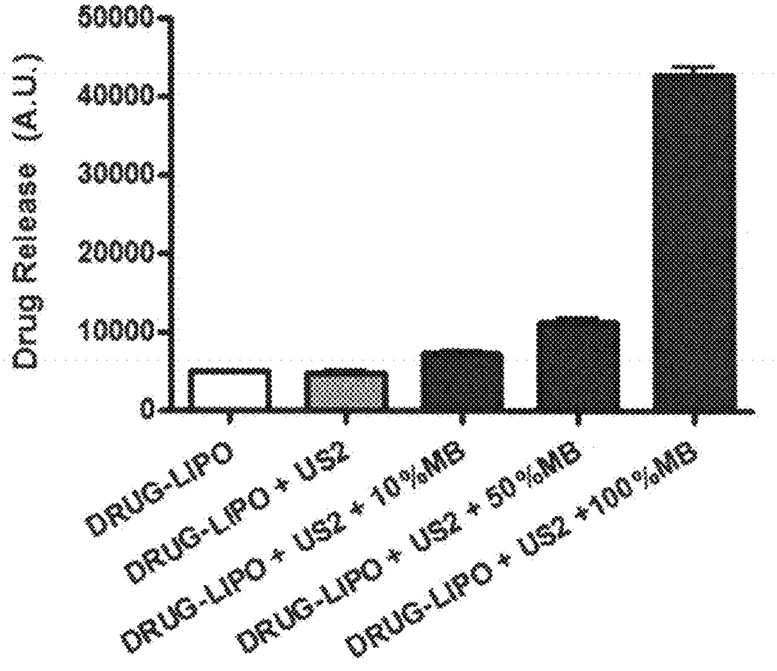
FIG. 3 In vitro ultrasound-mediated localized drug release from microbubble drug conjugates FIG. 4 In vivo rodent tumor model ultrasound and microbubble vascular disruption boost in immunotherapy efficacy
Figure 4:
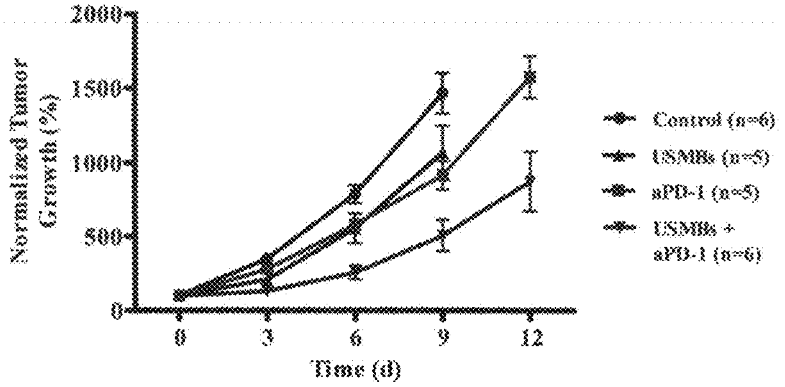
Figure 5:
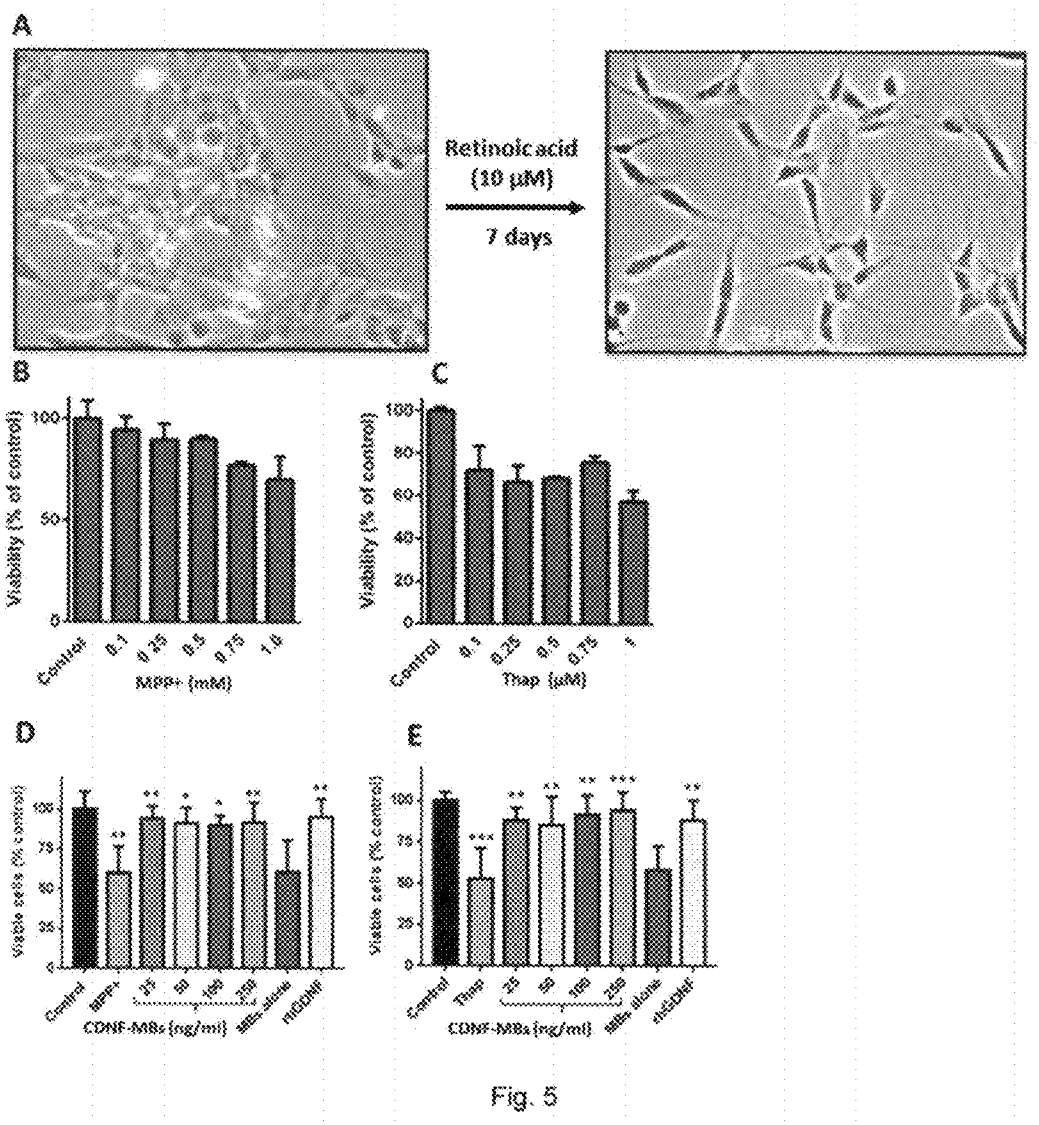
FIG. 5: Neuroprotective effects of CDNF microbubble drug conjugates (MDCs) against parkinsonian neurotoxins. Phase contrast photomicrographs of human SHSY-5Y cells differentiated with 10 mM retinoic acid into neuron-like cells (N type) with extended neurites (A); Neurotoxic effects of MPP+ (B) and (D) and neurotocix effects of thapsigargin (C) and (E). Recombinant human GDNF at 50 ng/ml was used as a positive control

Novel refinements were done to the microbubble generation to increase counts in order to improve in vivo performance for anticipated clinical use. FIGS. 2-3 shows Coulter count results with modified microfluidic geometry used for microbubble generation (capillary tube lengths and diameters). FIG. 4 shows Coulter count results with modified PFC (perfluorocarbon) gas quantity. FIG. 5 shows Coulter counts in combination experiments where different microfluidics for microbubble generation (red and purple), at varying air volumes, and varying quantities of DSPC lipid (40-70 mg) in the formulation were tested.

Example 3: Cy5.5 Labeling of Lipid Vesicle Solution

The lipid vesicles prepared as described in Example 1 were functionalized with Cy5.5 prior to microbubble formation.

Cy5.5 dye was conjugated to the lipid vesicles (Example 1). 200 μl of carbonate buffer (10% v/v) was added to 2 ml of lipid vesicle solution, followed by 1 μl (1× Cy5.5), 2 μl (2× Cy5.5), or 3 μl (3× Cy5.5) of NHSester Cy5.5 (10 μg/μl). The solution was mixed and the reaction allowed to proceed for 2 hr at room temperature. Free Cy5.5 was separated from the lipid vesicle-conjugated Cy5.5 using an Amicon 10 kDa cutoff concentrator. The Cy5.5-lipid vesicle solution volume was reduced to 1 ml.

A further example to label MDCs with a Cy5.5 is though click chemistry by incorporating a functionalized azide-PEG lipid to the lipid vesicles (Example 1) and then adding, mixing, and incubating the Cy5.5. dye. An Amicon concentrator may be used to remove unconjugated dye.

Example 4: Conjugation of Biologics to Lipid Vesicles

A common method for associating protein molecules (antibodies, ligands, proteins, Bispecific T cell engaging antibodies, antibodies with binding specificity to viral vector gene therapies, others) to microbubbles is by covalent linkage (also referred to as chemical conjugation). Chemical conjugation techniques are best to use for in vivo studies as they are stable in the blood and have proven successful when linking biologics to lipids. A variety of standard chemical conjugation reactions have been utilized in the literature, including attaching a peptide or protein via carbodiimide chemistry (Palmowski et al, 2008) or stable thioether bond chemistry (Anderson et al, 2010). Polymer spacers of various length, such as PEG, may be used to maintain distance between the protein and the microbubble shell (Kim et al, 2000).

Lipid vesicles comprised of DSPC plus DSPE-PEG (2000) amino linker were formulated as per Example 1.

Proteins were covalently attached directly to the functionalized, stable lipid vesicles in aqueous buffers prior to (perfluorocarbon) gas microbubble formation. The antibody's c-terminal carboxy group were chemically conjugated to the amine groups incorporated on the lipid vesicles. In this method, the antibody was attached to amine-PEG functionalized lipid vesicles prior to conversion to microbubbles; The antibody-lipid vesicles were then purified of unbound antibodies before being converted to microbubbles by incorporating gas into the vesicles.

Antibodies were dialyzed into MES (2-ethanesulfonic acid) buffer, followed by the addition of 1.1 mg sulfo-NHS (N-hydroxysulfosuccinimide) (final concentration 5 mM) and 0.4 mg EDC (final concentration 2 mM). The mixture was allowed to react for 15 min, after which it was purified with an Amicon 10 kDa cutoff using MES buffer; the solution volume was reduced to 100-200 μl. The free antibody was removed using an Amicon 100 kDa cutoff concentrator.

The inclusion of the biologics to the amine-PEG-DPSE lipid vesicles did not impact gas microbubble formation, the size of generated microbubbles, or their concentration or the bioactivity of the biologics (see example 9)

A further example to conjugate biologic drugs to MDCs is though click chemistry by incorporating a functionalized azide-PEG lipid to the lipid vesicles (Example 1) and then adding, mixing, and incubating, for example, an anti CTLA-4 antibody. Focused ultrasound can then be used with immunotherapy MDCs circulating through the bloodstream to disrupt the MDCs to increase drug concentration at tumors and to disrupt the tumor vasculature to further increase immunotherapy drug efficacy.

In a targeted diagnostic microbubble variant, a single domain antibody targeting IGFBP7 ($V_H$H 4.43, as described in WO2010043037A1) was conjugated to the lipid vesicles of Example 1 prior to microbubble formation.

Briefly, 1 mg $V_H$H 4.43 (~3 mg/ml) was dialized into MES buffer, followed by the addition of 1.1 mg sulfo-NHS (final concentration 5 mM) and 0.4 mg EDC (final concentration 2 mM). The mixture was allowed to react for 15 min, after which it was purified with an Amicon 10 kDa cutoff using MES buffer; the solution volume was reduced to 100-200 μl. The NHS-ester modified protein (100 μl) was mixed with carbonate (100 μl, 10%) and Cy5.5-labeled lipid solution (2-10 ml); the reaction was allowed to proceed for 2 hr. The free antibody was removed using an Amicon 100 kDa cutoff concentrator.

This method can be used to prepare both labelled and unlabeled antibody vesicles and to prepare labelled vesicles with a variety of dyes such as, for example, rhodamine.

Example 5. Conjugated Microbubble Formation from Labeled Lipid Vesicles

The lipid vesicles conjugated to Cy5.5 (Example 3) or $V_H$H 4.43 (Example 4) were converted to microbubbles, which were then characterized.

Briefly, the labelled lipid vesicles solution was mixed with gas (i.e. perfluorocarbon or air) and surfactant (i.e. tween80, stearic acid• or an alternative detergent) in a tube or cartridge. Vigorous mixing, pressure, and/or sonication was applied to convert liposomal solution to larger gas-filled microbubbles.

Alternatively, a bubble-generating apparatus may be used in an automated process to provide more reproducible microbubbles/results as described in the following patents assigned to Artenga Inc.:

'Microbubble Medical Devices' U.S. Pat. No. 8,679,051 issued Mar. 25, 2014.

'Medical Microbubble Generation' U.S. Pat. No. 8,257,338 issued Sep. 4, 2012

Example 6. Conjugated Microbubble Characterization

The conjugated microbubbles prepared in Example 5 were characterized using methods described in Example 2.

Table 3 shows absorbance measurements at 280 nm, 555 nm, and 678 nm. These results confirmed successful conjugation of antibody (280 nm), Cy5.5 (678 nm), Cy5.5-labeled antibody, and/or rhodamine-labeled antibody (555 nm) to the lipid vesicles in solution and maintenance of the link after gas microbubble formation.

TABLE 3

Summary of absorbance measurements for antibody and dye incorporation in lipid vesicles and microbubbles (MB).

| Construct | $A_{280}$ | $A_{555}$ | $A_{678}$ |
|---|---|---|---|
| 1x PEG lipid vesicle | 0.172 | 0.036 | 0.004 |
| 2x PEG lipid vesicle | 0.255 | 0.009 | 0.009 |
| 3x PEG lipid vesicle | 0.359 | 0.006 | 0.002 |
| 1x PEG Ab lipid vesicle | 2.879 | 0.019 | 0.002 |
| 1x PEG Rhod Ab lipid vesicle | 3.468 | 2.510 | 0.066 |
| 1x PEG 1x Cy5.5 lipid vesicle | 0.802 | 0.181 | 0.511 |
| 1x PEG 2x Cy5.5 lipid vesicle | 0.820 | 0.106 | 1.960 |
| 1x PEG 3x Cy5.5 lipid vesicle | 0.884 | 0.150 | 2.963 |
| 3x PEG Rhod Ab lipid vesicle and 1x Cy5.5 | 1.207 | 0.488 | 1.603 |
| 3x PEG Rhod Ab lipid vesicle and 1x Cy5.5 | 1.21 | 0.608 | 1.501 |
| 1x PEG MB | −0.241 | −0.226 | −0.077 |
| 1x PEG Ab MB | 0.987 | 0.053 | −0.025 |
| 1x PEG Rhod Ab MB | 1.425 | 0.909 | 0.038 |
| 1x PEG MB 2x Cy5.5 | 0.419 | 0.048 | 0.710 |
| 1x PEG MB 3x Cy5.5 | 0.420 | 0.080 | 1.120 |
| 3x PEG lipid vesicle | 0.536 | 0.001 | 0.020 |
| 3x PEG Cy5.5 protein lipid vesicle (no purification) | 1.719 | 0.009 | 0.481 |
| 3x PEG Cy5.5 protein lipid vesicle (with purification) | 1.079 | 0.004 | 0.357 |

Results for Cy5.5-conjugated microbubbles (Table 4) show that chemical attachment of 1×, 2× or 3× fluorescent Cy5.5 onto the external shell of amine-PEG-DSPE-containing lipid vesicles prior to gas microbubble formation did not impact gas microbubble formation, size or concentration of generated microbubbles.

TABLE 4

Coulter counter results of microbubble size/concentration distribution in Cy5.5-conjugated microbubbles with 3X PEG amine linker. Total microbubble counts/ml: $3.546 \times 10^8$ (1x Cy5.5); $2.892 \times 10^8$ (2x Cy5.5); $1.690 \times 10^8$ (3x Cy5.5).

| Size µM | 1X [C]/mL | 2X [C]/mL | 3X [C]/mL |
|---|---|---|---|
| 0.75-1.00 | $2.120 \times 10^8$ | $1.806 \times 10^8$ | 9.234E+07 |
| 1.01-2.00 | $9.550 \times 10^7$ | $7.150 \times 10^7$ | $5.725 \times 10^7$ |
| 2.01-3.00 | $3.770 \times 10^7$ | $3.051 \times 10^7$ | $1.745 \times 10^7$ |
| 3.01-4.00 | $9.126 \times 10^6$ | $5.943 \times 10^6$ | $1.613 \times 10^6$ |
| 4.01-5.00 | $1.106 \times 10^5$ | $5.414 \times 10^5$ | $2.889 \times 10^5$ |
| 5.01-6.00 | $9.797 \times 10^4$ | $4.899 \times 10^4$ | $6.818 \times 10^4$ |
| 6.01-7.00 | $1.212 \times 10^4$ | $6.565 \times 10^3$ | $2.576 \times 10^4$ |
| 7.01-15.00 | $5.555 \times 10^3$ | $4.040 \times 10^3$ | $1.162 \times 10^4$ |
| 15.01-30.00 | 0.000 | 0.000 | 0.000 |

Tables 5 and 6 show the size distribution for various microbubble preparations. Chemical conjugation of Rhodamine-labeled or unlabeled antibody, in addition to chemical conjugation of Cy5.5, onto the external shell of amine-PEG-DSPE-containing lipid vesicles prior to gas microbubble formation did not impact gas microbubble formation, size, or concentration of generated microbubbles.

TABLE 5

Coulter counter results of microbubble size/concentration distribution in 1x Cy5.5-conjugated microbubbles with 3X PEG amine linker ($3.546 \times 10^8$/ml); 1x Cy5.5- and Rhod-Ab-conjugated microbubbles with 3X PEG amine linker ($4.814 \times 10^8$/ml); and 1x Cy5.5- and Ab-conjugated microbubbles with 3X PEG amine linker ($2.769 \times 10^8$/ml).

| Size µM | 3x PEG 1x Cy5.5 MB | 3x PEG 1x Cy5.5 Rhod Ab MB | 3x PEG 1x Cy5.5 Ab MB |
|---|---|---|---|
| 0.75-1.00 | $2.120 \times 10^8$ | $2.966 \times 10^8$ | $1.623 \times 10^8$ |
| 1.01-2.00 | $9.550 \times 10^7$ | $1.423 \times 10^8$ | $7.917 \times 10^7$ |
| 2.01-3.00 | $3.770 \times 10^7$ | $3.476 \times 10^7$ | $2.888 \times 10^7$ |
| 3.01-4.00 | $9.126 \times 10^6$ | $7.298 \times 10^6$ | $5.938 \times 10^6$ |
| 4.01-5.00 | $1.106 \times 10^5$ | $4.338 \times 10^5$ | $5.449 \times 10^5$ |
| 5.01-6.00 | $9.797 \times 10^4$ | $3.838 \times 10^4$ | $7.979 \times 10^4$ |
| 6.01-7.00 | $1.212 \times 10^4$ | $1.010 \times 10^4$ | $9.090 \times 10^3$ |
| 7.01-15.00 | $5.555 \times 10^3$ | $6.060 \times 10^3$ | $8.585 \times 10^3$ |
| 15.01-30.00 | 0.000 | 0.000 | 0.000 |

TABLE 6

Coulter counter results of microbubble size/concentration distribution in microbubbles with 3X PEG amine linker ($4.128 \times 10^8$/ml); and 1x Cy5.5-Ab-conjugated microbubbles with 3X PEG amine linker with ($3.645 \times 10^8$/ml) or without ($1.082 \times 10^9$/ml) purification of protein from lipid vesicles.

| Size µM | 3x PEG MB | 3x PEG 1x Cy5.5 Ab MB (no purification) | 3x PEG 1x Cy5.5 Ab MB (purification) |
|---|---|---|---|
| 0.75-1.00 | $2.626 \times 10^8$ | $8.643 \times 10^8$ | $2.487 \times 10^8$ |
| 1.01-2.00 | $1.008 \times 10^8$ | $1.809 \times 10^8$ | $8.669 \times 10^7$ |
| 2.01-3.00 | $4.095 \times 10^7$ | $3.089 \times 10^7$ | $2.439 \times 10^7$ |
| 3.01-4.00 | $7.872 \times 10^6$ | $5.584 \times 10^6$ | $4.301 \times 10^6$ |
| 4.01-5.00 | $5.378 \times 10^5$ | $2.909 \times 10^5$ | $3.934 \times 10^5$ |
| 5.01-6.00 | $3.485 \times 10^4$ | $2.576 \times 10^4$ | $5.202 \times 10^4$ |
| 6.01-7.00 | $5.555 \times 10^3$ | $2.525 \times 10^3$ | $1.061 \times 10^4$ |
| 7.01-15.00 | $5.050 \times 10^2$ | $1.515 \times 10^3$ | $3.535 \times 10^3$ |
| 15.01-30.00 | 0.000 | $1.515 \times 10^3$ | 0.000 |

Example 7. Conjugated Microbubble Payload Delivery Using Ultrasound

Figure 6:
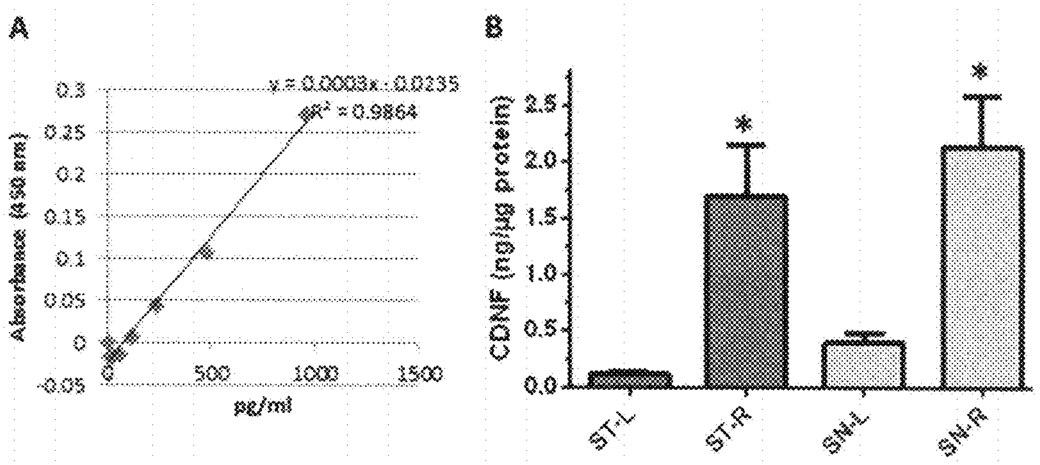
FIG. 6: ELISA quantification of targeted in vivo delivery of CDNE protein to the striatum (ST) and substantia nigra (SN) using microbubble drug conjugates and MR guided focused ultrasound. Sonications were targeted to the right brain hemisphere (ST-R, SN-R) with the left brain hemisphere serving as a control.

Using surface plasmon resonance (SPR). FIG. 6 demonstrates in vitro the enhanced, on demand release of drug from drug loaded liposomes (drug-lipo) using microbubbles (10-100% MB concentrations) and ultrasound (US2). In a clinical application this would permit highly localized drug delivery with controlled drug release.

Microbubble drug conjugate surrogates were prepared as described in Example 5 with a fluorescent dye payload and injected in tumor-bearing rodent models and ultrasound exposures applied locally to the tumors. Optical imaging (GE Healthcare explore Optix) was used to demonstrate enhanced perfusion and retention in vivo of microbubble payload in tumor bearing rodent models. In a clinical application this would permit enhanced perfusion and retention of drug from microbubble drug conjugates. In a clinical application using approved focused ultrasound systems capable of precision targeting of diseased regions of the body (including but not limited to tumors) this would permit high dose, localized drug delivery with enhanced perfusion and delivery.

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

Example 8: Production of Microbubble Drug Conjugates and Targeted Microbubbles

The lipid vesicle production of Example 1, conjugation of biologics to lipid vesicles and purifying the solution without the need of an organic solvent of Example 4, and microbubble generation of Example 2, were done using high lipid concentrations (30 mg lipids per 10 ml solution for example) whereby the resulting solution produced therapeutically relevant quantities of microbubble drug conjugates.

Different lipid-drug linking modalities may be incorporated in the liposome solution such as covalent (amine, carboxyl, others), electrostatic (cationic, anionic), 'click chemistry' (azide, cyclooctyne, others), or biotin-avidin conjugation of the liposomes to the drug.

The present invention is a method to produce an MDC solution whereby a biologic drug's bioactivity is maintained post conjugation as shown in Example 9. The simple, one step process described avoids the cost, complexity, and potential sterility compromise of producing and then mixing separate MDC and DLL solutions prior to infusion.

- MDCs can be used with FUS for non-invasive, targeted, and temporary BBB opening of diseased brain regions for active drug transport and greater drug perfusion as shown in Example 10
- Ultrasound manipulation of circulating microbubbles can increase immunotherapy efficacy for cancer patients without the added toxicity typically associated with combining other drugs or treatments through:
  - Promoting the release of tumor antigens, modulating the tumor microenvironment, and increasing cytotoxic T-cells (Lui et al (J Trans Medicine, 2012) and Hunt et al (J Ultrasound Med, 2015))
  - Boosting checkpoint inhibitor efficacy (tumor eradication and an active immune response) by slowing or stopping blood flow within a tumor (David E. Goertz, et al 'Enhancing Checkpoint Inhibitor Therapy with Ultrasound Stimulated Microbubbles' Ultrasound in Med.&Biol., Vol. 00, No. 00, pp. 1_14, 2018)

A preferred embodiment of the invention to produce and administer MDC solutions is described below:

A checkpoint inhibitor antibody (anti PD-1, anti PDL-1, or anti CTLA-4) that is an ineffective monotherapy once cancer spreads to the brain is conjugated to lipid vesicles as described in Examples 1 and 4, using high lipid concentrations and microbubble generation of Example 2, thereby producing a solution of therapeutically relevant quantities of microbubble drug conjugates.

The MDC solution is administered intravenously and circulates throughout the bloodstream. Focused ultrasound (FUS) is used to target brain tumors and sonication rapidly compresses and expands the MDCs at the frequency of the FUS. The resulting mechanical action temporarily opens the tight endothelial junctions that form the blood brain barrier (BBB) and promotes release of antibodies from the MDCs for active drug transport into tumors with enhanced perfusion.

Figure 7:
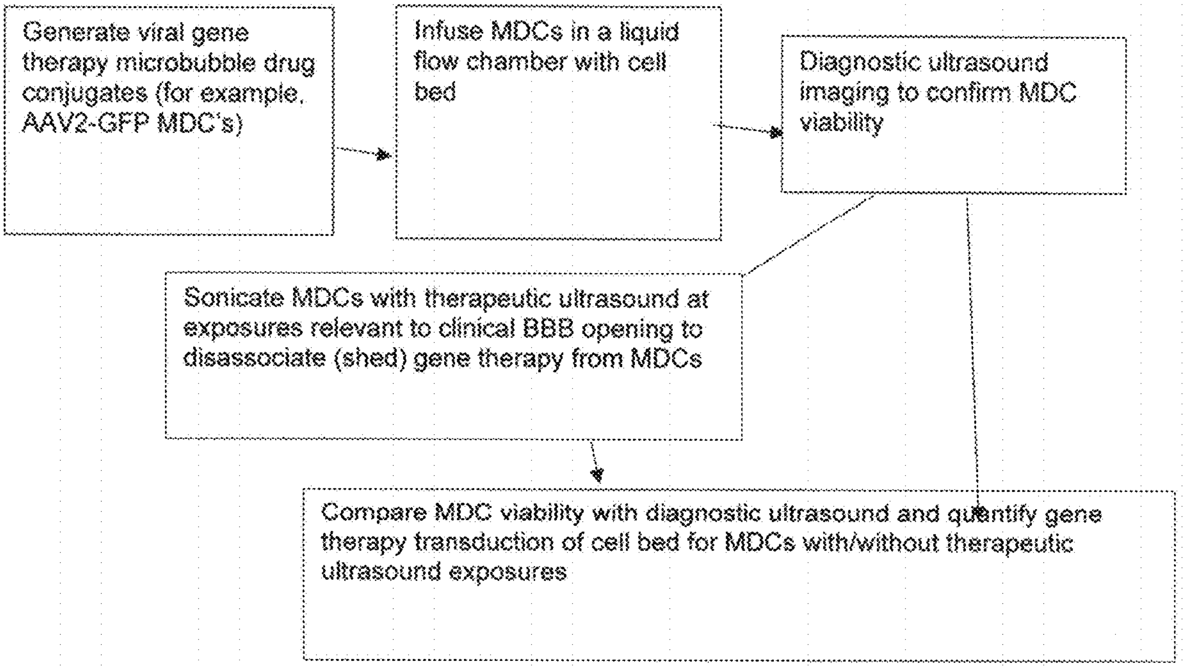
FIG. 7: Flow chart of in vitro flow chamber experimental procedure to confirm on demand disassociation of viral gene therapy from microbubble drug conjugates and cell bed transduction using therapeutic ultrasound exposures FIG. 8 In vitro flow chamber GFP transduction comparison of viral gene therapy microbubble drug conjugates with/without ultrasound FIG. 9 In vitro GFP transduction of viral gene therapy microbubble drug conjugates comparing MDCs featuring antibody linkers (6G6, 3F8, and 4C10) with varying binding specificity to AAV2

The FUS acoustic pressure is then increased and ultrasound exposures modified in order to induce MDC expansions and contractions sufficient to slow or stop blood flow within the tumors. This mechanical action has a synergistic effect to promote tumor reduction (as shown in FIG. 7) and immune response activation as well as releasing additional drug within the tumor. Reference: Goertz D, et al 'Enhancing Checkpoint Inhibitor Therapy with Ultrasound Stimulated Microbubbles' Ultrasound in Med. & Biol., Vol. 00, No. 00, pp. 1_14, 2018)

The BBB starts closing immediately after the few minutes of FUS sonications cease but remains open for a few hours sufficient for small molecule drug delivery.

MDCs that are not disrupted by FUS exposures circulate and clear in the standard way of ultrasound contrast agent microbubbles used for diagnosis: the PFC gas leaks from the MDCs and is expelled through the lungs and the collapsed lipid microbubble shells with conjugated antibodies is cleared by the liver's Kupffer cells. This liver clearance will prevent system wide dosing and potential endocrine immune-related adverse effects.

The therapy described in this embodiment can also be used on other indications such as primary triple negative breast cancer, ovarian, liver, pancreatic cancers, and others. MDC solutions can be produced with a variety of biologics including antibody fragments, targeted therapy, bispecific T cell engaging antibodies (BiTEs), and others.

Example 9: Bioactivity Confirmation of Microbubble Drug Conjugates

Cerebral Dopamine Neurotrophic factor (CDNF) protein (a Parkinson's Disease neuroprotective drug) was used to produce CDNF: MDCs and the retention of the neuroprotective activity of CDNF-MDCs confirmed in vitro.

Figure 8:
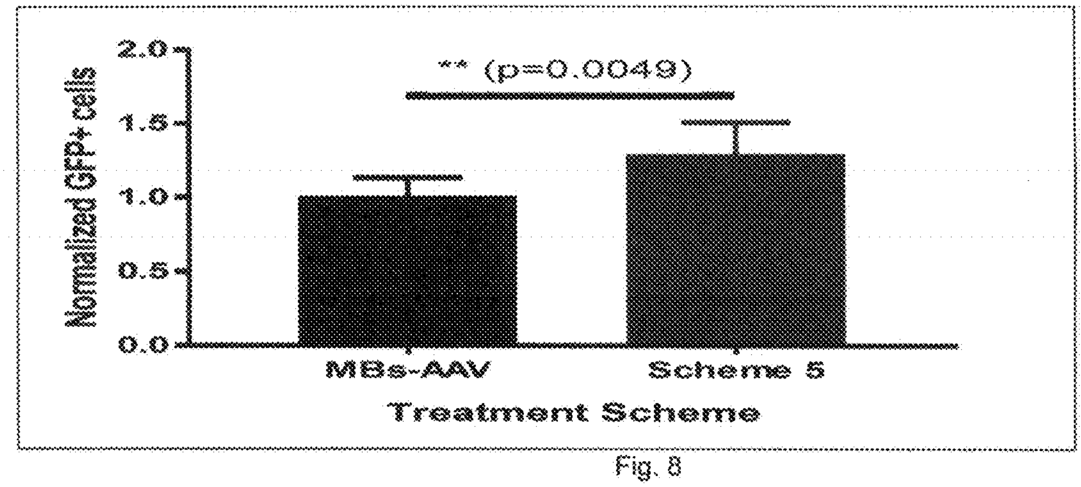

Neuroprotection was tested in the well-established neuronal model of human SHSY-5Y cells (Lopes, F. M., et al. (2010) *Brain Res.* 1337, 85-94) treated with parkinsonian neurotoxins. Human SHSY-5Y cells were grown in 24 well dishes and differentiated into neuron-like cells by treatment with 10 μM retinoic acid (RA) for 7 days (FIG. 8A). The differentiated cells extended neurites, expressed the neuronal markers MAP2 and beta-III tubulin as well as the dopamine cell marker, tyrosine hydroxylase (not shown).

The neurotoxic effects of MPP+ (active metabolite of MPTP) and thapsigargin (thap, ER stress inducer) were first established by treating the cells with 0.1-1.0 mM MPP+ or 0.1-1.0 μM thap for ~16 h. Cell viability was quantified by the CFDA assay as described previously (Sandhu, J. K., et al. (2009) *Neurobiol. Dis.* 33, 405-414.).

Recombinant human GDNF at 50 ng/ml was used as a positive control. Cells pre-incubated for 2 hours with 50 ng/ml rhGDNF before exposure and during the treatment with either 1.0 mM MPP+ or 1.0 μM thapsigargin were protected from cell death (FIGS. 8D and 8E).

The neuroprotective effects of CDNF-MDCs was tested using a similar protocol (as described above for rhGDNF) by treating cells with 1.0 mM MPP+ or 1.0 UM thap for ~16 h in the absence or presence of 25-250 ng/ml CDNF-MDCs. The pre-treatment with 25-250 ng/ml CDNF-MDCs completely protected the cells from the neurotoxic effects of MPP+ (FIG. 8D) and thapsigargin (FIG. 8E). A similar level of neuroprotection was obtained with CDNF-MDCs concentrations in the range of 25-250 ng/ml for both MPP+ and thapsigargin.

These results demonstrate that CDNF retains its biological activity after conjugation to microbubbles. The neurotoxic effects of MPP+ or thapsigargin were abolished in cells treated in the presence of CDNF-MDCs. Maximum neuroprotection was reached at concentrations ranging from 25-250 ng/ml.

Example 10: Microbubble Drug Conjugate and Focused Ultrasound Blood Brain Barrier Opening for Non-Invasive, Targeted Drug Delivery to the Brain Focused ultrasound (FUS) can be used to target deep seated brain regions and compress and expand microbubbles in circulation. This temporarily opens the tight vascular endothelial cell junctions of the blood brain barrier (BBB) to permit active drug transport. Microbubbles are essential to open the BBB with FUS at lower, safe acoustic pressures.

AAV2-GFP MDCs were injected into healthy rodents and FUS sonications used to open the BBB in the two brain regions affected by Parkinson's disease, the striatum (ST) and substantia nigra (SN). MR contrast agent gadolinium was co-injected and MR imaging performed to confirm BBB opening in the two regions.

Figure 9:
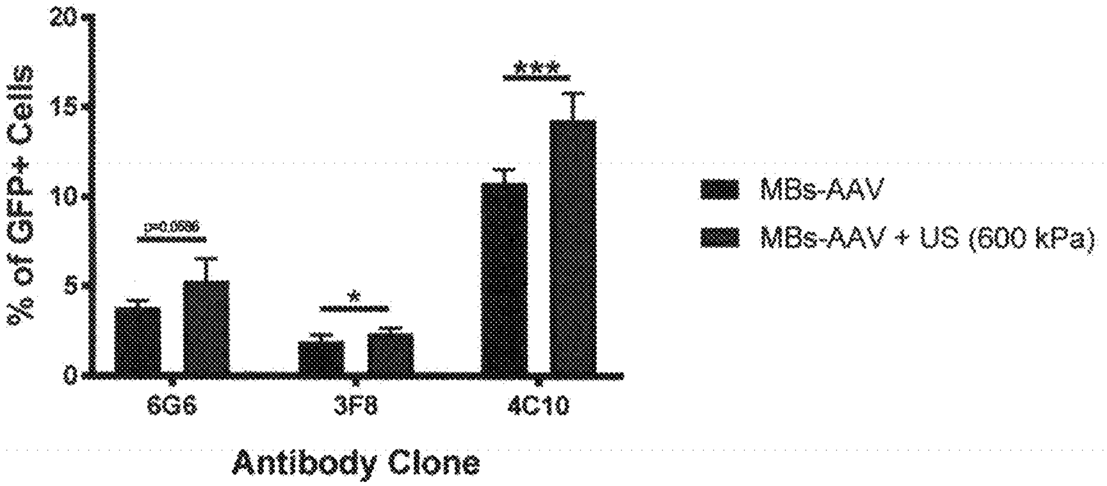

CDNF protein neurotrophic drug was conjugated to MDCs and delivered to the SN and ST in this manner. Only one hemisphere was sonicated so the animals acted as their own control. See FIG. 9 ELISA tissue analysis confirming significant CDNF concentration delivered to the sonicated hemispheres of the ST and SN vs. non-sonicated.

Example 12: Production of Microbubble Drug Conjugate Viral Vector Gene Therapy Linkers The Mouse Rapid Prime immunization approach was used to generate mouse hybridomas secreting IgG monoclonal antibodies specific for adeno-associated virus 2 (AAV2).

Immunizations were performed with whole virus on female BALB/c mice with a total of $2*10^{11}$ recombinant AAV2-GFP per mouse over the immunization period for cell fusion and hybridoma cell line generation. Lymphocytes collected from immunized mice were harvested and counted and fused with murine SP2/0 myeloma cells in the presence of poly-ethylene glycol. The fusion product of up to $10^8$ lymphocytes were cultured using a single step cloning method (HAT selection) and remaining fusion product frozen and stored in liquid nitrogen as backup.

Indirect ELISAs were used to screen for hybridomas that bind to AAV2 and custom downstream assays, including affinity testing and viral neutralization assays, were used to test for antibodies with a range of affinities and properties.

Clones were transferred to cell wells and grown in HT containing medium. Primary screening was performed by indirect ELISA on whole live AAV2-GFP probing with secondary antibody for both IgG and IgM isotypes. Cultures were retested separately on AAV2-GFP and recombinant AAV5-GFP antigens, the later as a specificity control. Positive hybridomas were isotyped for IgF, IgM, and IgA.

Twenty different mouse anti AAV2 protein purified monoclonal antibodies were produced by hybridoma. Ten were assessed, for binding affinity, to AAV2 by calculating the ratio of virus/trapping Elisa with three fold titrations as shown in Table 7 below.

TABLE 7

Anti-AAV2 Antibody Binding Affinity

| | | | | | | |
|---|---|---|---|---|---|---|
| Title: | Titration of anti-AAV2 Mouse Hybridomas on AAV2 antigen by Indirect ELISA and by Antibody Trapping ELISA | | | | | |
| Date: | Nov. 24 2017 | | | | | |
| SOP Reference: | IPASOP-G-15b | | | Top 10 | | |
| Operator: | K. M. McIntosh | 1E6 | 2B2 | 3H3 | 3H4 | 4C10 |
| Data reviewed by: | D. R. Kroeger | 4D1 | 5A8 | 5H11 | 6G6 | 9D4 |
| Antigen: | AAV2, Goat anti-mouse(g/m(H + L) | | | | | |
| Source of Primary Antibody: | current culture - mid log growth | | | | | |
| ELISA Conditions: | | | | | | |

Corning Costar 96 well ELISA plates coated with:
AAV2 at 10^8 viral genome units per well in Carbonate Coating Buffer (pH 9.6) at 100 μl/well ON at 4 C.
Blocked with 3% Skim Milk Powder in PBS (pH 7.6) at 100 μl/well for 1 hour at RT with shaking
Primary antibody: TC sup neat at 100 uL/well, incubate for 1 hour at 37 C. with shaking
Secondary Antibody 1:5000 Goat anti-mouse IgGγ-HRP Homemade mix at 100 uL/well in PBS-Tween at 37 C. w/shaking TABLE 7-continued Anti-AAV2 Antibody Binding Affinity All washing steps performed for 30 mins with PBS-Tween
TMB Substrate added at 50 uL/well, developed in the dark and stopped with equal volume 1M HCl
Development time: 9 mins
Plate read at 450 nm
Antibody Trap Conditions:

Primary antibody: Hybridoma TC sup neat at 100 μL/well for 1 hour at Room Temperature with shaking
Corning Costar 96 well ELISA plates coated with:
1:10000 Goat anti-Mouse IgG/IgM(H + L) in Carbonate Coating Buffer (pH 9.6) at 100 μL/well in PBS (pH 7.4) O/N at 4 C.
No Blocking
Primary antibody: Hybridoma TC sup neat at 100 μL/well for 1 hour at Room Temperature with shaking
Secondary Antibody 1:5000 Goat anti-mouse IgGγ-HRP Homemade mix at 100 uL/well in PBS-Tween at RT w/shaking
All washing steps performed for 30 mins with PBS-Tween
TMB Substrate added at 50 μL/well, developed in the dark and stopped with equal volume 1M HCl
Development time: 3 mins
Plate read at 450 nm

| | | AAV21 0D > 0.20 Antibody Titration | | | | | |
|---|---|---|---|---|---|---|---|
| | | 1E6 1 | 2B2 2 | 2E9 3 | 2F4 4 | 2H5 5 | 3C3 6 |
| Neat | A | 0.49 | 0.414 | 0.411 | 0.386 | 0.324 | 0.316 |
| 1:3 | B | 0.465 | 0.4 | 0.346 | 0.328 | 0.299 | 0.323 |
| 1:9 | C | 0.48 | 0.387 | 0.231 | 0.206 | 0.313 | 0.279 |
| 1:27 | D | 0.468 | 0.42 | 0.157 | 0.145 | 0.32 | 0.183 |
| 1:81 | E | 0.26 | 0.345 | 0.105 | 0.099 | 0.241 | 0.11 |
| 1:243 | F | 0.128 | 0.226 | 0.087 | 0.082 | 0.155 | 0.083 |
| 1:729 | G | 0.082 | 0.137 | 0.064 | 0.07 | 0.101 | 0.062 |
| 1:2187 | H | 0.125 | 0.115 | 0.072 | 0.07 | 0.092 | 0.07 |

| | | AAV21 0D > 0.20 Antibody Titration | | | | | | |
|---|---|---|---|---|---|---|---|---|
| | | 3H3 7 | 3H4 8 | 4C10 9 | 4D1 10 | PBS 11 | Controls 12 | |
| Neat | A | 0.505 | 0.501 | 0.377 | 0.496 | 0.068 | 0.084 | IgG Non Secretor |
| 1:3 | B | 0.498 | 0.493 | 0.379 | 0.466 | 0.056 | 0.097 | IgG1 Secretor |
| 1:9 | C | 0.519 | 0.496 | 0.325 | 0.469 | 0.055 | 0.075 | IgG2a Secretor |
| 1:27 | D | 0.542 | 0.533 | 0.269 | 0.46 | 0.055 | 0.072 | IgM Secretor |
| 1:81 | E | 0.559 | 0.531 | 0.157 | 0.231 | 0.056 | 0.242 | 1/500 Serum |
| 1:243 | F | 0.509 | 0.5 | 0.096 | 0.106 | 0.051 | 0.065 | 1/500 PreImmune Serum |
| 1:729 | G | 0.382 | 0.383 | 0.066 | 0.075 | 0.053 | 0.072 | |
| 1:2187 | H | 0.204 | 0.208 | 0.077 | 0.076 | 0.074 | 0.095 | |

Selected clones were then subcloned by plating parental clones into single cell colonies and antibody purified from culture supernatants using protein G columns. Purified antibody is stored in a carrier-free neutral low endotoxin buffer containing no azide.

The same MDC antibody linker development process can be used to produce MDC linkers for other adeno-associated virus (AAV) vector serotypes (AAV1, AAV9 etc.) with controllably varying binding affinities. It can be used to develop MDC antibody linkers for other viral vectors (adenovirus, oncolytic viruses, retrovirus; herpesvirus, etc.) and used to develop binding/neutralizing antibody linkers (BNAbs) as shown in Example 15.

Example 13: Production and Characterization of Viral Gene Therapy Microbubble Drug Conjugates The following is a preferred example of a means to conjugate viral based gene therapy to microbubbles for targeted, non-invasive delivery to the brain and other organs. A variety of gene therapies and indications, including oncology, neurodegenerative disorders, and others may be treated using this method.

Six antibodies with varying binding affinity to AAV2 were selected for MDC configuration. The lipid vesicle production of Example 1 and conjugation of antibodies to lipid vesicles and purification of Example 4 were done. Antibody loading was quantified as shown in Table 8.

TABLE 8

Antibody Loading of Lipid Vesicle Solution

| Anti-AAV2 Mab bio-conjugation to LPN1X microbubble solution. Antibody | 2018 May 6 Protein in 2 ml solution (mg) |
|---|---|
| 3H3 | 0.474 |
| 9D4 | 0.263 |
| 4C10 | 0.428 |
| 6G6 | 0.223 |
| 2E9 | 0.406 |
| 3F8 | 0.532 |

Microbubble generation of Example 2 was done for each antibody. The microbubble solution was centrifuged, isolated, and resuspended with 2 ml phosphate buffered saline (PBS) to remove excess shell lipids. 100 μl at ($6 \times 10^{12}$ virus molecules/mL) of AAV2-GFP (green fluorescent protein gene therapy surrogate) was added to the solution and the solution inverted and incubated for 15 minutes to promote binding.

The AAV2-SIRT3 microbubbles were centrifuged, isolated, and resuspended with PBS three times to remove remaining 99.9% of the buffer liquid and unbound AAV2-SIRT3 to produce AAV2-GFP MDCs.

Figure 10:
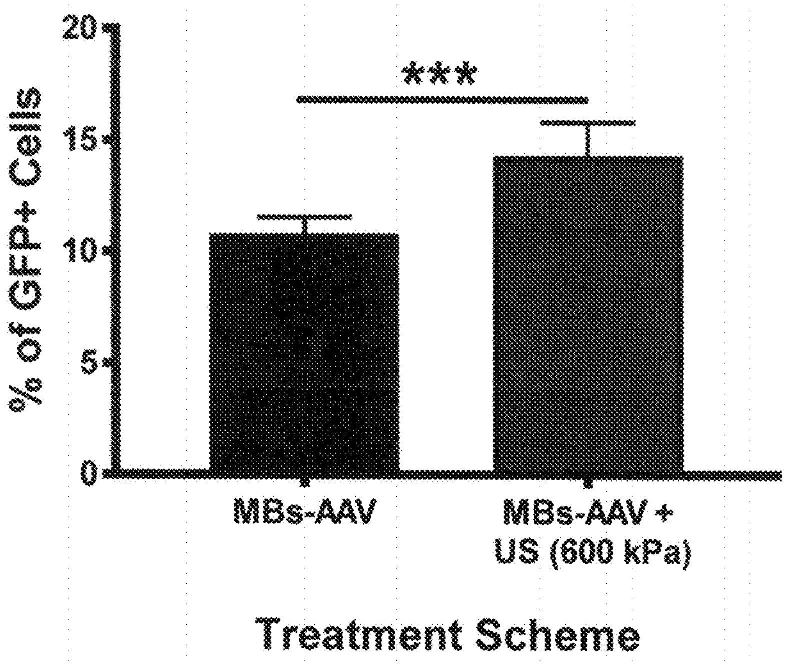
FIG. 10 In vitro GFP transduction of viral gene therapy microbubble drug conjugates with 4C10 antibody linker with/without ultrasound FIG. 11 Flow chart of in vivo AAV2-SIRT3 microbubble drug conjugate and focused ultrasound non-invasive blood brain barrier delivery to rodent striatum FIG. 12 Diagnositc tumor-targeting microbubble schematic with IGFBP7 binding specificity to HCC liver tumors. The targeting microbubble is comprised of a perfluorocarbon gas 12.1, lipid shell 12.2, and targeting ligands 12.3 conjugated to the shell surface. The ligands can target molecules expressed on endothelial cells surface or thrombus, for example IGFBP7.

In vitro experiments (see FIG. 10 experimental apparatus) were done with AAV2-GFP MDCs to confirm gene therapy bioactivity and that focused ultrasound (FUS) can be used to induce dissociation of AAV2 from MDCs in a controllable manner:

- We demonstrated using cell-based flow cytometry that focused ultrasound exposures relevant to clinically scalable BBB opening and drug delivery can promote the release of AAV gene therapy from MDCs to permit localized transfection (p=0.049 and p=0.0586 AAV MDC only control vs. AAV MDC and FUS)—see 'Normalized 6G6 and 3F8' and '6G6 MDC' results below.
- AAV2 GFP bioactivity was maintained after conjugation to microbubbles loaded with antibody linkers and FUS exposures. Four different linkers (4C10, 2E9, 9D9, and 6G6)• with a range of AAV2 binding affinities were used with varying FUS pressures (300 KPa, 600 KPa, and 900 KPa).

Figure 11:
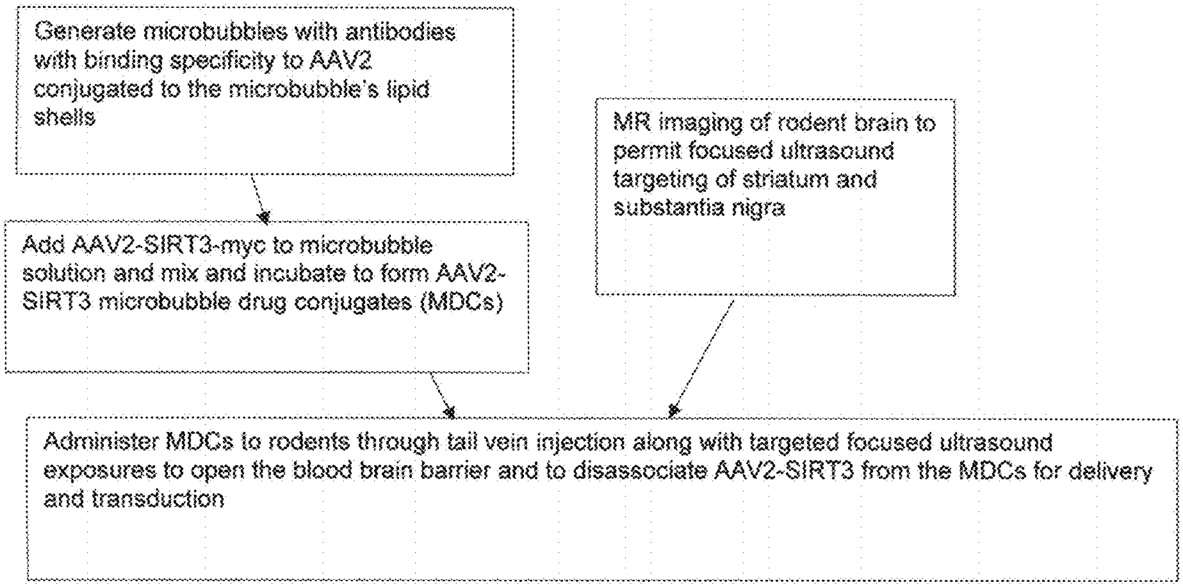
Figure 12:
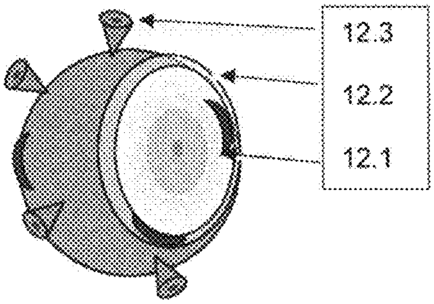
Figure 13:
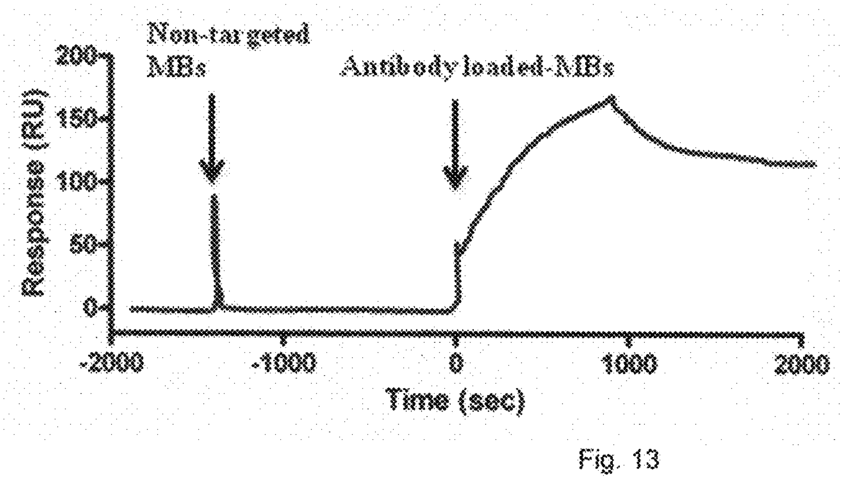
FIG. 13 HCC liver tumor targeting microbubbles vs. non-targeting microbubbles in vitro cell bed

Our findings (FIGS. 11, 12 and 13) along with previous FUS/MDC targeted BBB opening and localized drug delivery experiments suggest the potential to induce genetic changes in diseased regions of the brain while avoiding peripheral side effects We compared the percent of GFP transfected cells with MDCs versus MDCs and ultrasound for different AAV2 antibody linkers. We see a statistically significant increase in transfection with the ultrasound groups indicating that FUS can be used to release viral gene therapy from MDCs at diseased regions in vivo. Three antibody linkers (6G6, 3F8, & 4C10) were tested and the 4C10 linker selected for the in vivo experiments had the highest transfection as well as highest yield (data not shown).

NORMALIZED 6G6 AND 3F8 MDC'S

Testing of 6G6 Cartridge (2019)

| Trial # 1 (Scheme 3 values) AAV2-GFP MDCs | Trial # 1 (Scheme 5 values) AAV2-GFP MDCs & FUS | Trial # 1 (Scheme 3 normalized) (3.81) | Trial # 1 (Scheme 5 normalized) (3.81) |
|---|---|---|---|
| 4.18 | 3.83 | 1.10 | 1.00 |
| 3.47 | 5.22 | 0.91 | 1.37 |
| 4.06 | 5.33 | 1.07 | 1.40 |
| 3.52 | 6.85 | 0.92 | 1.80 |

Testing of 3F8 Cartridge (2019)

| Trial # 2 (Scheme 3 values) AAV2 = GFP MDCs | Trial # 2 (Scheme 5 values) AAV2 GFP MDCs & FUS | Trial # 2 (Scheme 3 normalized) (1.92) | Trial # 2 (Scheme 5 normalized) (1.92) |
|---|---|---|---|
| 1.48 | 2.11 | 0.77 | 1.10 |
| 2.06 | 2.67 | 1.07 | 1.39 |
| 2.29 | 2.70 | 1.19 | 1.41 |
| 1.84 | 1.85 | 0.96 | 0.97 |
| | 2.55 | | 1.33 |
| | 2.34 | | 1.22 |
| | 2.39 | | 1.25 |
| | 2.20 | | 1.15 |

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

Example 13: Viral Gene Therapy Microbubble Drug Conjugate Non-invasive, Targeted Blood Brain Barrier Delivery Sirtuin 3 (SIRT3) gene therapy has been shown to rescue neurons in alpha synuclein rodent models of Parkinson's disease (Nash, J. E., et al, Neurobiol. Dis 106 (2018) 133-146) so AAV2-SIRT3 microbubble drug conjugates (MDCs) were developed as a potential clinical treatment for Parkinson's disease as follows:

The lipid vesicle production of Example 1, the production of 4C10 antibody linker with binding specificity to AAV2 of Example 12, the conjugation of antibodies to lipid vesicles and purification of Example 4, and microbubble generation of Example 2, and AAV2-SIRT3 conjugation of Example 13 was done to produce AAV2-SIRT3-MDCs.

Tail vein injection of AAV2-SIRT3-MDCs in healthy rodents was done and focused ultrasound used to temporarily open the BBB and disassociate the viral gene therapy for active transport of AAV2-SIRT3 to the brain. MR imaging with gadolinium confirmed bright regions where FUS targeted the brain, indicating BBB permeabilization. FIG. 14 illustrates the experiment schematic.

Post treatments, rodent brain tissue was harvested and cryosectioned for immunofluorescent analysis. Immunofluorescence labeling and imaging confirmed SIRT3 expression in the ipsilateral striatum using the following antibodies: Myc (SIRT3 myc), SIRT3 (endogenous and ectopic SIRT3), and DAPI (nucleus).

Reference: Dennison Trinh, Joanne Nash, David Goertz, Kullervo Hynynen, Sharshi Bulner, Umar Iqbal & James Keenan (2022) Microbubble drug conjugate and focused ultrasound blood brain barrier delivery of AAV-2 SIRT-3, Drug Delivery, 29:1, 1176-1183, DOI: 10.1080/10717544.2022.2035855.

The embodiments and examples described herein are illustrative and are not meant to limit the scope of the invention as claimed. Variations of the foregoing embodiments, including alternatives, modifications and equivalents, are intended by the inventor to be encompassed by the claims. Furthermore, the discussed combination of features might not be necessary for the inventive solution.

Example 14: Production of and Treatment Methods for Viral Gene Therapy MDCs With Neutralizing Antibody Linkers Microbubbles in circulation clear from the body as the gas leaks from the microbubbles to be expelled by the lungs and the deflated lipid shells are primarily cleared in the liver by resident Kupffer cell macrophages. Viral gene therapy microbubble drug conjugates cleared in this manner will result in gene therapy transduction of healthy liver tissue. Dependant upon the dose delivered and the toxicity of the gene therapy this may induce adverse effects.

Therefore, there exists the need for viral gene therapy MDCs whereby the gene therapy cannot transduce while conjugated to the microbubble shells. Only after disassociation from the microbubble at diseased regions of the body using focused ultrasound would transduction and permanent genetic changes be possible.

Viral-neutralizing antibody therapeutics have been developed to treat SARS-COV-2 and Covid-19.

In a preferred embodiment of Example 12 of the viral gene therapy MDC invention antibodies that preferentially bind to as well as neutralize specific viral vectors are developed by hybridoma as described in Example 11.

The antibody linker may be selected on the basis of its capacity to neutralize vectors through, for example, binding affinity to the viral cell surface proteins needed for the virus to enter a cell to permit transduction.

Neutralization assays will be used to select antibodies to evaluate as MDCs and to confirm that MDC configuration neutralizes viral vector transduction capacity using in vitro cell well assays.

Antibodies with binding specificity and neutralizing capability may be developed for different adeno-associated vector serotypes (AAV1, AAV9 etc.) and other viral vectors used for gene therapy such as adenovirus, oncolytic viruses, retrovirus, or herpesvirus.

The lipid vesicle production of Example 1, covalent conjugation of viral binding and neutralizing antibodies to lipid vesicles of Example 4, microbubble generation of Example 5, and viral gene therapy conjugation of Example 12 will be done to produce viral gene therapy MDCs whereby the gene therapy in neutralized while conjugated to the microbubbles.

Antibodies with varying binding affinity strengths will be conjugated to MDCS and assessed using an in vitro flow chamber as described in Example 12 and with in vivo delivery and biodistribution characterization as shown in Example 13. The binding affinity selected will be sufficiently strong to ensure that all but trace quantities of gene therapy remain conjugated to the MDCs in circulation but still permit the dissociation of viral gene therapy from the MDCs using ultrasound exposures at clinically safe ultrasound parameters including acoustic pressure. An example of typical parameters would be 1 MZ frequency, peak negative pressure of 0.15 and 0.30 MPa, pulse length of 10 ms, and pulse repetition frequency of 1 Hz.

For clinical treatments the viral gene therapy microbubble drug conjugates will be intravenously infused in the blood stream and circulate while focused ultrasound is used to resonate and/or disrupt the microbubbles in order to disassociate the viral gene therapy at diseased regions of the body for localized transduction and treatment. Diseased regions of most organs in the body are amenable to focused ultrasound treatment including the brain with FUS and MDC targeted, non-invasive, and temporary BBB opening as per Example 10.

The embodiments and examples described herein are illustrative and are not meant to limit the scope of the invention as claimed. Variations of the foregoing embodiments, including alternatives, modifications and equivalents, are intended by the inventor to be encompassed by the claims. Furthermore, the discussed combination of features might not be necessary for the inventive solution.

Example 15: Production of Small Molecule Drug and Microbubble Conjugates

Microbubble drug conjugates featuring small molecule drugs are produced whereby the drug is first reacted with lipid powders to form powdered lipids linked to small molecules. Lipid vesicles are then produced as described in Example 1 by combining the small molecule drug lipid with a second lipid (DSPC, DBPC, others) followed by emulsification, and the addition of liquid buffer (PBS, others). The solution is then purified using a high performance liquid chromatography (HPLC) column and small molecule microbubble drug conjugates generated as per Example 5.

Example 16: Production of Disease-Targeting Microbubbles for Diagnosis with In Vitro and In Vivo Characterization Imaging with ultrasound contrast agent (USCA) microbubbles is used clinically to diagnose, for example, liver tumors. USCA imaging typically has a minimum detection limit of, for example, lesions 2 cm in length or greater. Reducing the detection limit in order to detect microtumors would improve outcome for patients and hence there is a need for microbubbles that target to and bind to microtumors and other diseased regions.

Approved Insulin-like growth factor-binding protein 7 (IGFBP7) is a protein involved in several cancers including Hepatocellular carcinoma (HCC). IGFBP7 targeting antibodies were developed and covalently conjugated to microbubbles as illustrated in FIG. 15.

Preclincally, fluorescently labeled IGFBP7 were injected intravenously into rodent HCC models and histology performed to confirm IGFBP7 expression.

Ultrasound imaging was used to compare the IV injection of tumor-targeting IGFBP7 antibody microbubbles versus non-targeted microbubbles. Ultrasound imaging confirmed significantly greater contrast enhancement with the targeted microbubbles and that the targeted microbubbles binding to the tumors persisted in vivo longer than non-targeted microbubbles in circulation.

FIG. 16 shows in vitro targeted microbubble results comparing nontargeted and antibody targeted microbubbles for retention to tumor cell bed in Biocore flow chamber

Information Disclosure Sheet

U.S. Pat. No. 6,245,318 Klibanov, Selectively binding ultrasound contrast agents;

U.S. Pat. No. 7,452,551 Unger E, Targeted compositions for diagnostic and therapeutic use U.S. Pat. No. 6,723,303 Quay S (2004) Ultrasound contrast agents including protein stabilized microspheres of perfluoropropane, perfluorobutane, or perfluoropentane U.S. Pat. No. 7,452,551•Unger E, Targeted compositions for diagnostic and therapeutic use (Unger invented Definity MBs, and started Imarx therapeutic MBs who's IP is now owned by Cerevast)

Evan Unger: U.S. Pat. No. 7,329,402 Methods of imaging and treatment and U.S. Pat. No. 6,521,211 Methods of imaging and treatment with targeted compositions. Assignee: Bristol-Myers Squibb U.S. Pat. No. 8,263,739 Von Wronski, Tweedle, et al, Compounds for targeting endothelial cells, compositions containing the same and methods for their use. Assignee Bracco From the same team U.S. Pat. Nos. 7,884,183, 7,820,621

U.S. Pat. No. 7,211,248 Davidson M, Enhancement of transfection of DNA into the liver, Assignee Sonogene U.S. Pat. No. 6,264,917 Klaveness J, Targeted ultrasound contrast agents U.S. Pat. No. 11,007,284 Holland C, Gas-encapsulated acoustically responsive stabilized microbubbles and methods for treating cardiovascular disease U.S. Pat. No. 10,058,837 borden m, systems, methods, and devices for production of gas-filled microbubbles

The invention claimed is:

1. A method of producing lipid-shelled microbubble drug conjugates (MDCs) for viral gene therapy, comprising:

a) providing an antibody having binding specificity to a viral vector;

b) conjugating the antibody to one or more functionalized lipids to form antibody-lipid conjugates;

c) generating lipid-shelled microbubbles comprising the antibody-lipid conjugates on the microbubble shell surface; and d) associating a viral gene therapy vector with the antibody on the microbubble shell to form viral gene therapy MDCs;

wherein the viral vector is selected from the group consisting of adeno-associated viral vectors, adenoviral vectors, lentiviral vectors, herpes simplex viral vectors, retroviral vectors, and oncolytic viral vectors;

and wherein the antibody binds the viral vector and associates the viral vector with the lipid-shelled microbubble.

2. A method for optimizing association between a viral gene therapy vector and a viral gene therapy microbubble drug conjugate (MDC) produced according to the method of claim 1, comprising:

a) providing a plurality of antibodies having different binding strengths to a viral vector;

b) producing a plurality of viral gene therapy MDCs using the antibodies;

c) exposing the MDCs to ultrasound under conditions sufficient to disrupt, oscillate, or otherwise activate the microbubbles;

d) determining release of the viral vector from the MDCs and transduction of target cells by the released viral vector; and e) selecting an antibody having a binding strength that maintains association of the viral vector with the MDC during circulation and permits ultrasound-mediated release of the viral vector while maintaining viral transduction activity.

3. The method of claim 2, wherein the antibody comprises a viral vector-binding domain that binds a surface epitope of the viral vector and inhibits or reduces receptor-mediated cellular entry of the viral vector while the viral vector remains associated with the lipid-shelled microbubble during systemic circulation, thereby reducing off-target transduction prior to ultrasound-mediated release of the viral vector at a target treatment site.

* * * * *